US007125705B2

(12) United States Patent
Colosi

(10) Patent No.: US 7,125,705 B2
(45) Date of Patent: Oct. 24, 2006

(54) POLYNUCLEOTIDES FOR USE IN RECOMBINANT ADENO-ASSOCIATED VIRUS VIRION PRODUCTION

(75) Inventor: Peter Colosi, Alameda, CA (US)

(73) Assignee: Genzyme Corporation, Cambridge, MA (US)

( * ) Notice: Subject to any disclaimer, the term of this patent is extended or adjusted under 35 U.S.C. 154(b) by 913 days.

(21) Appl. No.: 09/839,583

(22) Filed: Apr. 20, 2001

(65) Prior Publication Data
US 2002/0052485 A1    May 2, 2002

Related U.S. Application Data

(60) Provisional application No. 60/200,453, filed on Apr. 28, 2000.

(51) Int. Cl.
*C12N 7/00* (2006.01)
*C12N 15/00* (2006.01)
*C12N 5/10* (2006.01)
*C07H 21/04* (2006.01)

(52) U.S. Cl. ............... 435/235.1; 435/369; 435/320.1; 536/23.1; 536/23.72

(58) Field of Classification Search .................... None
See application file for complete search history.

(56) References Cited

U.S. PATENT DOCUMENTS

| 5,830,725 | A | * | 11/1998 | Nolan et al. | ............... | 435/455 |
| 5,872,005 | A | | 2/1999 | Wang et al. | | |
| 6,686,200 | B1 | * | 2/2004 | Dong et al. | ............... | 435/457 |
| 2005/0169892 | A1 | * | 8/2005 | Johnson | ..................... | 424/93.2 |

FOREIGN PATENT DOCUMENTS

| WO | WO 96/40240 | 12/1996 |
| WO | WO 97/09441 A | 3/1997 |
| WO | WO 00/22152 A | 4/2000 |

OTHER PUBLICATIONS

Massie et al. Improved adenovirus vector provides herpes simplex virus ribonucleotide reductase R1 and R2 subunits very efficiently. Biotechnology (N Y). vol. 13, No. 6, pp. 602-608, Jun. 1995.*
No et al. Ecdysone-inducible gene expression in mammalian cells and transgenic mice. Proc Natl Acad Sci U S A. vol. 93, No. 8, pp. 3346-3351, Apr. 1996.*
Xiao et al. Production of high-titer recombinant adeno-associated virus vectors in the absence of helper adenovirus. J. Virol. vol. 72, No. 3, pp. 2224-2232, Mar. 1998.*
Inoue et al. Packaging cells based on inducible gene amplification for the production of adeno-associated virus vectors. J Virol. vol. 72, No. 9, pp. 7024-7031, Sep. 1998.*
Samulski et al. Adenovirus E1B 55-Mr polypeptide facilitates timely cytoplasmic accumulation of adeno-associated virus mRNAs. J Virol. vol. 62, No. 1, pp. 206-210, Jan. 1988.*
Carter, "Adeno-Associated Virus Helper Functions," *Handbook of Paroviruses* 1(13):255-282 (1990).

Carter et al., "Properties of an Adenovirus Type 2 Mutant, Ad2dl807, Having a Deletion Near the Right-hand Genome Terminus: Failure to Help AAV Replication," *Virology* 126:505-516 (1983).
Georg-Fries et al., "Analysis of Proteins, Helper Dependence, and Seroepidemiology of a New Human Parovirus," *Virology* 134:64-71 (1984).
Handa, "Complementation of Adeno-Associated Virus Growth with Temperature-Sensitive Mutants of Human Adenovirus Types 12 and 5," *J. Gen. Virol.* 29:239-242 (1975).
Ito, M., "Adeno-associated Satellite Virus Growth Supported by a Temperature-sensitive Mutant of Human Adenovirus," *J. Gen. Virol.* 9:243-245 (1970).
Janik et al., "Locations of Adenovirus Genes Required for the Replication of Adenovirus-associated Virus," *Proc. Natl. Acad. Sci.USA* 78 (3):1925-1929 (1981).
Jay et al., "Eukaryotic Translational Control: Adeno-associated Virus Protein Synthesis is Affected by a Mutation in the Adenovirus DNA-binding Protein," *Proc. Natl. Acad. SCI. USA* 78(5):2927-2931 (1981).
Laughlin et al., "Effect of Deletions in Adenovirus Early Region 1 Genes Upon Replication of Adeno-Associated Virus," *J. Virol.* 41(3):868-876 (1982).
Myers et al., "Adeno-Associated Virus Replication. The Effect of $_L$-Canavanine or a Helper Virus Mutation on Accumulation of Viral Capsids and Progeny Single-Stranded DNA," *J. Biol. Chem.* 256(2):567-570 (1981).
Myers et al., "Adenovirus Helper Function for Growth of Adeno-Associated Virus: Effect of Temperature-Sensitive Mutations in Adenovirus Early Gene Region 2," *J. Virol.* 35(1):65-75 (1980).
Ostrove et al., "Adenovirus Early Region 1b Gene Function Required for Rescue of Latent Adeno-Associated Virus," *Virology* 104:502-505 (1980).
Richardson et al., "A cascade of Adenovirus Early Functions is Required for Expression of Adeno-Associated Virus," *Cell* 27(2):133-141 (1981).
Straus et al., "DNA-Minus Temperature-Sensitive Mutants of Adenovirus Type 5 Help Adenovirus-Associated Virus Replication," *J. Virology* 17:140-148 (1976).
Wang et al., "A Packaging Cell Line for Propagation of Recombinant Adenovirus Vectors Containing Two Lethal Gene-Region Deletions," *Gene Therapy* 2:775-783 (1995).
Matsushita et al. (1998) "Adeno-associated virus vectors can be efficiently produced without helper virus," *Gene Therapy*, 5(7):938-945.

* cited by examiner

*Primary Examiner*—Celine Qian
*Assistant Examiner*—Jennifer Dunston
(74) *Attorney, Agent, or Firm*—Robins & Pasternak LLP

(57) ABSTRACT

Accessory functions capable of supporting efficient recombinant AAV (rAAV) virion production in a suitable host cell are provided. The accessory functions are in the form of one or more vectors that are capable of being transferred between cells. Methods of producing rAAV virions are also provided. The methods can be practiced to produce commercially significant levels of rAAV particles without also generating significant levels of infectious helper virus or other contaminating by-products.

18 Claims, 8 Drawing Sheets

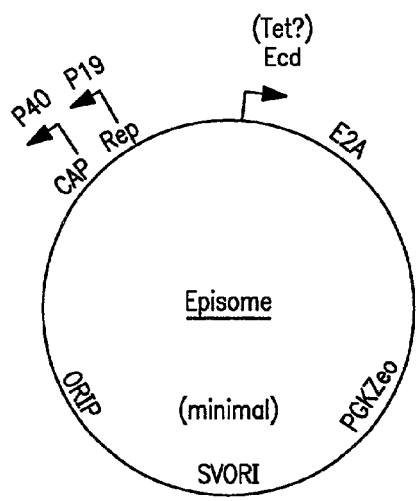
Genome Site 1
Genome Site 2
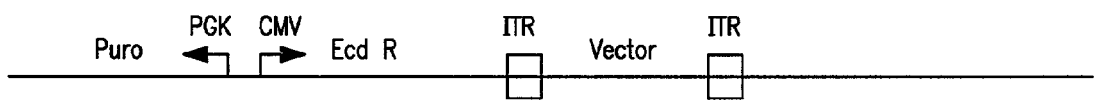
FIG. 6 ized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, *Current Topics in Microbiol. and Immunol.* 158:97–129 (1992). For descriptions of the construction of recombinant AAV virions see, e.g., U.S. Pat. Nos. 5,173,414 and 5,139,941; International Publication Numbers WO 92/01070 (published 23 Jan. 1992) and WO 93/03769 (published 4 Mar. 1993); Lebkowski et al., *Molec. Cell. Biol.* 8:3988–3996 (1988); Vincent et al., *Vaccines* 90 (Cold Spring Harbor Laboratory Press 1990); Carter, *Current Opinion in Biotechnology* 3:533–539 (1992); Muzyczka, *Current Topics in Microbiol. and Immunol.* 158:97–129 (1992); Kotin, *Human Gene Therapy* 5:793–801 (1994).

POLYNUCLEOTIDES FOR USE IN RECOMBINANT ADENO-ASSOCIATED VIRUS VIRION PRODUCTION

CROSS-REFERENCE TO RELATED APPLICATION

This application is related to provisional patent application Ser. No. 60/200,453, filed Apr. 28, 2000, from which priority is claimed under 35 USC §119(e)(1) and which is incorporated herein by reference in its entirety.

FIELD OF THE INVENTION

The present invention relates generally to methods and compositions for use in adeno-associated virus ("AAV") virion production. More particularly, the invention relates to constructs which provide accessory functions capable of supporting efficient AAV virion production in a suitable host cell and methods of use thereof.

TECHNICAL BACKGROUND

Gene delivery is a promising method for the treatment of acquired and inherited diseases. A number of viral-based systems for gene transfer purposes have been described, such as retroviral systems, which are currently the most widely used viral vector systems for this purpose. For descriptions of various retroviral systems, see, e.g., U.S. Pat. No. 5,519,740; Miller & Rosman, *BioTechniques* 7:980–990 (1989); Miller, *Human Gene Therapy* 1:5–14 (1990);Scarpa et al., *Virology* 180:849–852 (1991); Burns et al., *Proc. Natl. Acad. Sci. USA* 90:8033–8037 (1993); Boris-Lawrie & Temin, *Cur. Opin. Genet. Develop.* 3:102–109 (1993).

Adeno-associated virus (AAV) systems have also been used for gene delivery. AAV is generally considered a good choice for gene delivery because it has not been associated with any human or animal disease and does not appear to alter the biological properties of the host cell upon integration. AAV, which belongs to the genus Dependovirus, is a helper-dependent DNA parvovirus. Thus, in order for effective AAV virion production to occur, the host cell must also be infected with an unrelated helper virus, either adenovirus (Ad), a herpesvirus (HSV), or vaccinia virus. The helper virus supplies accessory functions that are necessary for most steps in AAV replication. In the absence of such infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful infection of such cells with a suitable helper virus. For example, human AAV will replicate in canine cells co-infected with a canine adenovirus. For a review of AAV, see, e.g., Berns & Bohenzky, *Advances in Virus Research* 32:243–307 (Academic Press, Inc. 1987).

The AAV genome is composed of a linear single-stranded DNA molecule which contains 4681 bases (B ems & Bohenzky, supra). The genome includes inverted terminal repeats (ITRs) at each end which function in cis as origins of DNA replication and as packaging signals for the virus. The ITRs are approximately 145 bp in length. The internal nonrepeated portion of the genome includes two large open reading frames, known as the AAV rep and cap regions, respectively. These regions code for the viral proteins involved in replication and packaging of the virion. In particular, a family of at least four viral proteins are synthe- Contemporary recombinant AAV (rAAV) virion production involves co-transfection of a host cell with an AAV vector plasmid usually containing one or more transgenes flanked by AAV ITRs, and a construct which provides AAV helper functions (e.g., rep and cap) to complement functions missing from the AAV vector plasmid. In this manner, the host cell is capable of expressing the AAV proteins necessary for AAV replication and packaging. To provide accessory functions, the host cell is then infected with a helper virus, typically an infectious adenovirus (type 2 or 5), or herpesvirus.

More particularly, AAV vector plasmids can be engineered to contain a functionally relevant nucleotide sequence of interest (e.g., a selected gene, antisense nucleic acid molecule, ribozyme, or the like) that is flanked by AAV ITRs which provide for AAV replication and packaging functions. After an AAV helper plasmid and an AAV vector plasmid bearing the nucleotide sequence are introduced into the host cell by transient transfection, the transfected cells can be infected with a helper virus, most typically an adenovirus, which, among other functions, transactivates the AAV promoters present on the helper plasmid that direct the transcription and translation of AAV rep and cap regions. Upon subsequent culture of the host cells, rAAV virions (harboring the nucleotide sequence of interest) and helper virus particles are produced.

When the host cell is harvested and a crude extract is produced, the resulting preparation will contain, among other components, approximately equal numbers of rAAV virion particles and infectious helper virions. rAAV virion particles can be purified away from most of the contaminating helper virus, unassembled viral proteins (from the helper virus and AAV capsid) and host cell proteins using known techniques.

Purified rAAV virion preparations that have been produced using infection with adenovirus type-2 contain high levels of contaminants. Particularly, 50% or greater of the total protein obtained in such rAAV virion preparations is free adenovirus fiber protein. Varying amounts of several unidentified adenoviral and host cell proteins are also present. Additionally, significant levels of infectious adenovirus virions are obtained, necessitating heat inactivation. The contaminating infectious adenovirus can be inactivated by heat treatment (56° C. for 1 hour) and rendered undetectable by sensitive adenovirus growth assays (e.g., by cytopathic effect (CPE) in a permissive cell line). However, heat treatment also results in an approximately 50% drop in the titer of functional rAAV virions.

Production of rAAV virions using an infectious helper virus (such as an adenovirus type-2, or a herpesvirus) to supply accessory functions is undesirable for several reasons. AAV vector production methods which employ a helper virus require the use and manipulation of large amounts of high titer infectious helper virus which presents a number of health and safety concerns, particularly in regard to the use of a herpesvirus. Selected herpes simplex virus type-1 (HSV-1) genes are significantly less efficient at supporting AAV replication than adenovirus- derived functions. Weindler et al., *J. Virol.* 65:2476–2483 (1991). In addition, some adenoviral proteins are cytotoxic or cytostatic to the host cell. For example, the E4ORF6 protein is toxic to cells in the presence of the E1B55k protein. Furthermore, concomitant production of helper virus particles in rAAV virion producing cells diverts large amounts of cellular resources away from rAAV virion production, possibly resulting in lower rAAV virion yields.

More particularly, in methods where infection of cells with adenovirus type-2 are used to provide the accessory functions, more than 95% of the contaminants found in the purified rAAV virion preparations are derived from adenovirus. The major contaminant, free adenovirus fiber protein, tends to co-purify with rAAV virions on CsCl density gradients due to a non-covalent association between the protein and rAAV virions. This association makes separation of the two especially difficult, lowering rAAV virion purification efficiency. Such contaminants may be particularly problematic since many adenoviral proteins, including the fiber protein, have been shown to be cytotoxic (usually at high concentrations), and thus may adversely affect or kill target cells. Thus, a method of producing rAAV virions without the use of infectious helper viruses to provide necessary accessory functions would be advantageous.

Because of the problems associated with the use of complete helper viruses, a number of researchers have investigated the genetic basis of accessory functions, particularly adenovirus- derived functions, in an attempt to derive functional helper constructs. Although many of the adenovirus ("Ad") or herpes simplex virus ("HSV") genes are incompletely mapped, it is known that Ad "early" genes are expressed before both the genes encoding the proteins necessary for replication and before the "late" genes. The early genes are divided into the following groups:

E1, E2, E4 and the VA RNAs. E1 is approximately 6 kb in size and encodes the E1A protein, the E1B19k protein, the E1B55k protein, and protein IX. A 72 kd E2A protein is encoded within E2, while E4ORF6 is encoded within the E4 region. It has been established that the E1B55k protein binds to both E4ORF6 and p53. Furthermore, the E4ORF6 protein is cytotoxic, but only in the presence of E1B55k.

It has been demonstrated that the full-complement of adenovirus genes are not required for accessory helper functions. In particular, adenovirus mutants incapable of DNA replication and late gene synthesis have been shown to be permissive for AAV replication. Ito et al., *J. Gen. Virol.* 9:243 (1970); Ishibashi et al, *Virology* 45:317 (1971). Similarly, mutants within the E2B and E3 regions have been shown to support AAV replication, indicating that the E2B and E3 regions are probably not involved in providing accessory functions. Carter et al., *Virology* 126:505 (1983). However, adenoviruses defective in the E1 region, or having a deleted E4 region, are unable to support AAV replication. Thus, E1A and E4 regions are likely required for AAV replication, either directly or indirectly. Laughlin et al., *J. Virol.* 41:868 (1982); Janik et al., *Proc. Natl. Acad. Sci. USA* 78:1925 (1981); Carter et al. (1983), supra). Other characterized Ad mutants include: E1B (Laughlin et al. (1982), supra; Janik et al. (1981), supra; Ostrove et al., *Virology* 104:502 (1980)); E2A (Handa et al., *J. Gen. Virol.* 29:239 (1975); Strauss et al., *J. Virol.* 17:140 (1976); Myers et al., *J. Virol.* 35:665 (1980); Jay et al., *Proc. Natl. Acad. Sci. USA* 78:2927 (1981); Myers et al., *J. Biol. Chem.* 256:567 (1981)); E2B (Carter, *Adeno-Associated Virus Helper Functions, in I CRC Handbook of Parvoviruses* (P. Tijssen ed., 1990)); E3 (Carter et al. (1983), supra); and E4 (Carter et al.(1983), supra; Carter (1995)). Although studies of the accessory functions provided by adenoviruses having mutations in the E1B coding region have produced conflicting results, Samulski et al., *J. Virol.* 62:206–210 (1988), recently reported that E1B55k is required for AAV virion production, while E1B19k is not. In addition, International Publication WO 97/17458 and Matshushita et al., *Gene Therapy* 5:938–945 (1998), describe accessory function vectors encoding various Ad genes.

Further characterization of the Ad genes required for helper functions has been attempted by transfecting various regions of the Ad genome and assessing virion production. Particularly, in vitro AAV replication has been assessed using human 293 cells transiently transfected with various combinations of adenovirus restriction fragments encoding single adenovirus genes or groups of genes. Janik et al. (1981), supra. Initial transfection studies were done in cells that stably express the adenovirus E1A and E1B regions, so the requirement for those regions could not be tested. However, it was deduced that the combination of three adenoviral gene regions, VA RNA, E2A and E4, could provide accessory functions (e.g., support AAV replication) at a level that was substantially above background, but that was still approximately 8,000 fold below the level provided by infection with adenovirus. When all combinations of two of the three genes were tested, the accessory function levels ranged between 10,000 to 100,000 fold below the levels provided by infection with adenovirus.

Accordingly, there remains a need in the art to identify a subset of the adenovirus genome or functional homologues of the adenovirus genome, that include only those accessory functions required for AAV vector production. Furthermore, if the required subset includes cytotoxic genes, there remains a need to control expression of these genes and resulting levels of the toxic gene product. The identification of the minimal complement of genes and modifications to control expression can be used to design constructs which, when introduced into a suitable cell line, allow for the selection of an AAV packaging cell line.

BRIEF SUMMARY OF THE INVENTION

The present invention is based on the identification of the minimal complement of genes necessary to provide accessory functions for efficient AAV vector production. The invention provides a system which identifies these genes, controls their expression and provides efficient production of AAV vectors.

In certain embodiments, the present invention provides nucleic acid molecules which provide one or more accessory functions for supporting rAAV virion production in a suitable host cell. Such molecules comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. The present invention also provides accessory function vectors comprising such nucleic acid molecules.

In certain other embodiments, the present invention provides accessory function vector systems comprising: a nucleic acid sequence that provides adenovirus VA RNAs, an adenovirus E4 ORF6 coding region, an adenovirus E2A 72 kD coding region, an adenovirus E1A coding region, and an adenovirus E1B region lacking an intact E1B55k coding region, which are included on more than one accessory function vector of said system. The present invention also provides host cells transfected with such accessory function vectors.

The present invention further provides methods of producing rAAV virions in which an AAV vector and an AAV helper construct comprising AAV coding regions, which are expressed in the host cell to complement AAV helper functions missing from the AAV vector, are introduced into a suitable host cell. An accessory function vector providing accessory functions for supporting efficient rAAV virion production is introduced into the host cell, and the host cell is cultured to produce rAAV virions.

The present invention further provides methods of producing rAAV virions comprising the steps of: introducing an AAV rep coding region and AAV vector sequences into a suitable host cell; infecting the host cell with a recombinant helper virus, wherein the recombinant helper virus comprises accessory functions and an AAV cap coding region; and culturing the host cell to produce rAAV virions. The AAV vector sequences may be introduced by transfection or by infection with a recombinant virus. In certain embodiments, the AAV vector sequences are episomal. In other embodiments, the AAV vector sequences are integrated into the host cell genome. The recombinant helper virus may be a recombinant adenovirus, which may be engineered such that the AAV cap coding region replaces the adenoviral E3 region.

The present invention also provides methods of producing rAAV virions comprising the steps of: introducing an AAV helper construct into a suitable host cell, said AAV helper construct comprising AAV coding regions that are expressed in the host cell to complement rAAV virion production in the host cell; introducing an accessory function system into the host cell, said accessory function system providing accessory functions for supporting rAAV virion production in the host cell; introducing an AAV vector by infection of the host cell; and culturing the host cell to produce rAAV virions. The AAV vector may be introduced into the host cell by infection with a recombinant AAV virion. The accessory function system may comprise an adenovirus VA RNA coding region, an adenovirus E4 ORF6 coding region, an adenovirus E2A 72kD coding region, an adenovirus E1A coding region, and an adenovirus E1B coding region. Furthermore, as discussed above, the E1B coding region may lack an intact E1B55k coding region.

The present invention also provides systems and methods for producing rAAV in which certain accessory and helper functions are located on a nucleic acid molecule that is maintained as an episome in the host cell. For example, AAV rep and cap coding regions and an adenoviral E2A coding region may be located on an episomal nucleic acid.

These and other embodiments of the subject invention will readily occur to those of ordinary skill in the art in view of the disclosure herein.

BRIEF SUMMARY OF THE DRAWINGS

FIG. 6 schematically illustrates the components of a system for the production of rAAV.

DETAILED DESCRIPTION OF THE INVENTION

Figure 1:
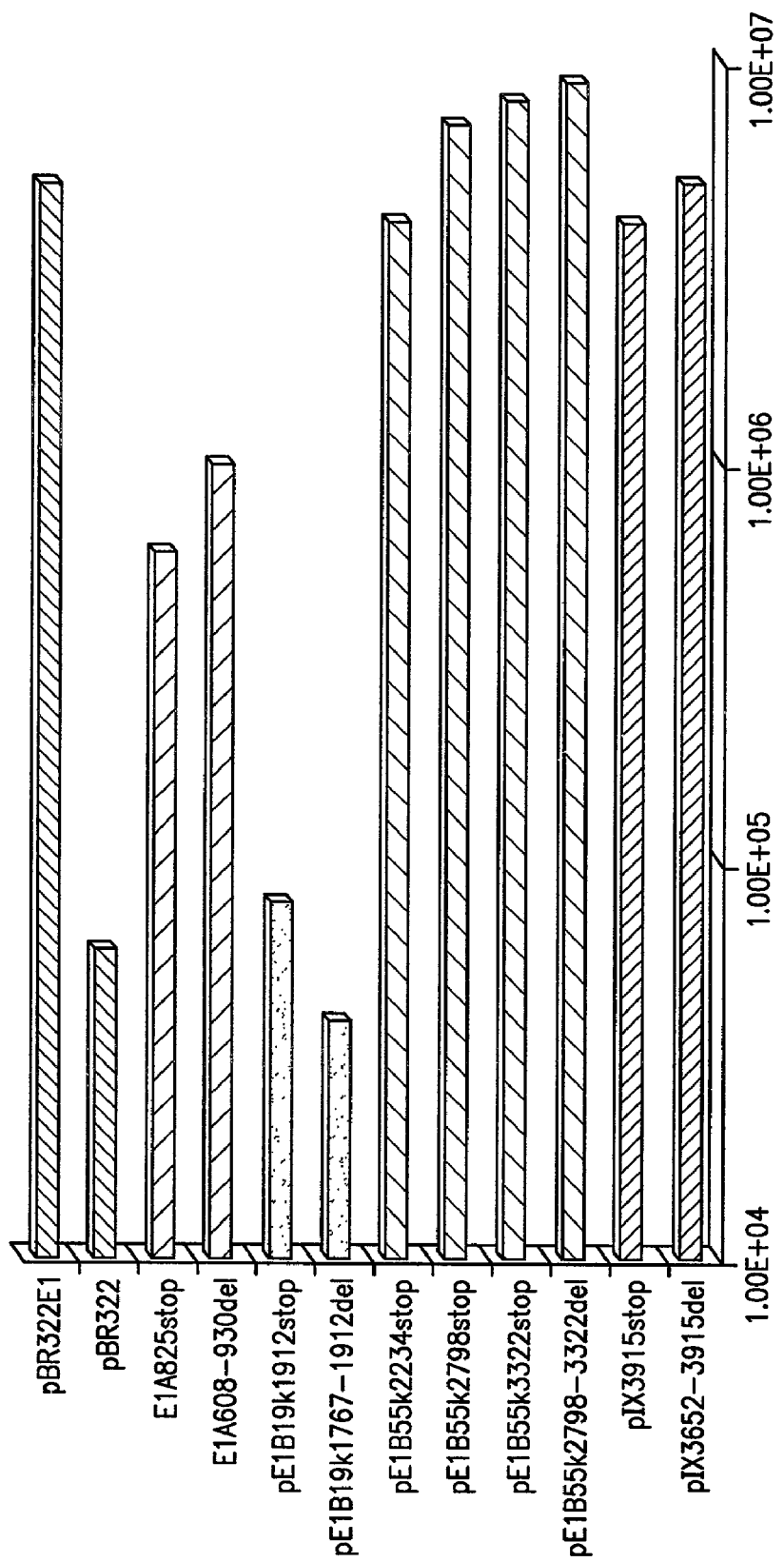
FIG. 1 depicts virion production by cells transfected with various Ad gene-containing plasmids. Deletions or mutations in E1B19k result in low levels of AAV virion production, comparable to the control plasmid, pBR322. The E1B19k mutated constructs result in at least 100-fold reduction in virion production as compared to other plasmids.
Figure 2:
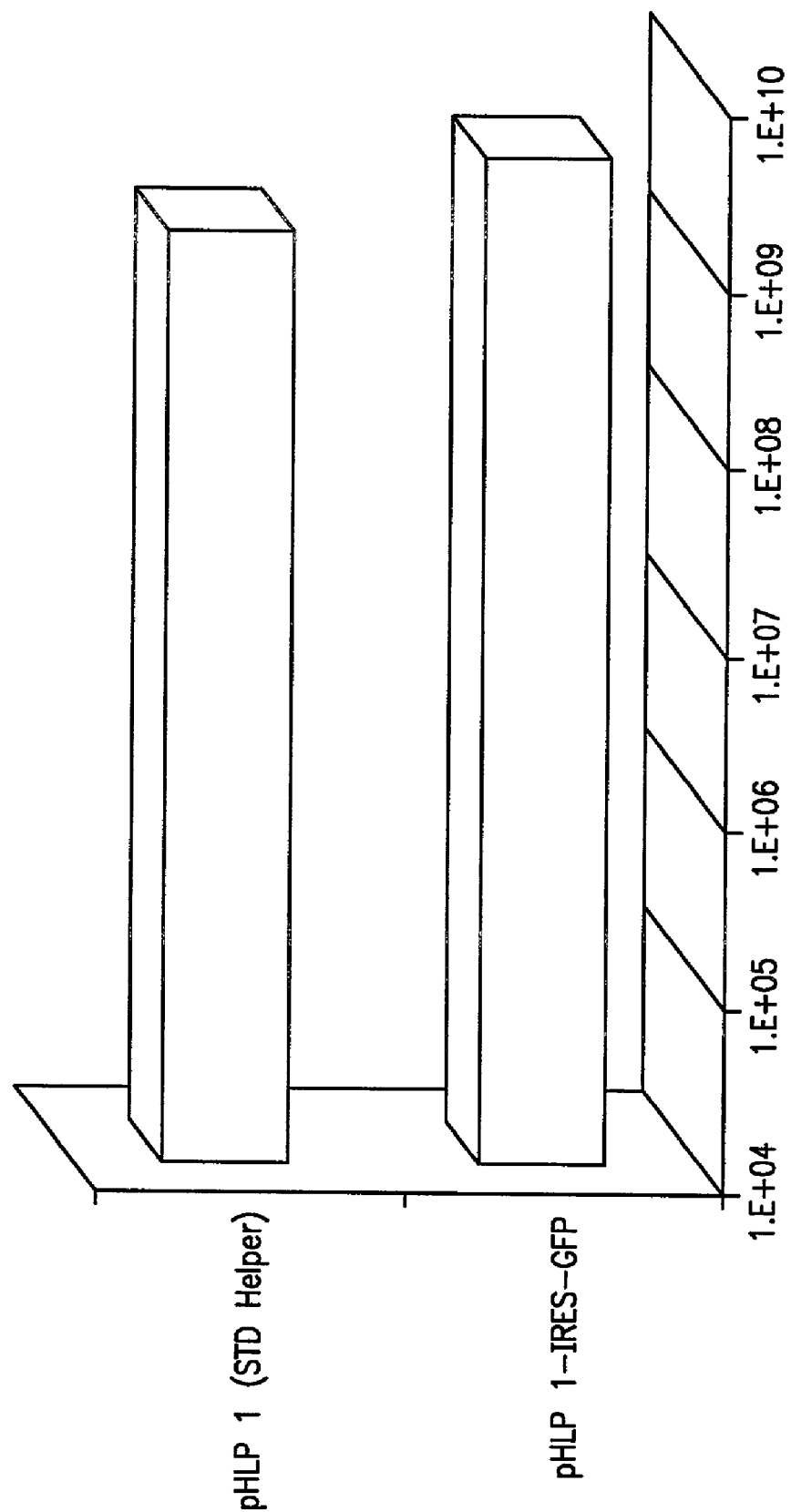
FIG. 2 depicts virion production by cells transfected with either pHLP 1 or pHLP 1-IRES-GFP.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al., *Molecular Cloning: A Laboratory Manual* (current edition); *I & II DNA Cloning: A Practical Approach* (D. Glover ed.); *Oligonucleotide Synthesis* (N. Gait ed., current edition); *Nucleic Acid Hybridization* (B. Hames & S. Higgins eds., current edition); *Transcription and Translation* (B. Hames & S. Higgins eds., current edition); *I & II CRC Handbook of Parvoviruses* (P. Tijessen ed.); *I & II Fundamental Virology*, (B. N. Fields and D. M. Knipe eds., 2d ed. 1991).

All publications, patents, and patent applications cited herein, whether supra or infra, are hereby incorporated by reference in their entirety.

As used in this specification and the appended claims, the singular forms "a, " "an" and "the" include plural references unless the content clearly dictates otherwise.

DEFINITIONS

In describing the present invention, the following terms will be employed, and are intended to be defined as indicated below.

"Gene transfer" or "gene delivery" refers to methods or systems for inserting foreign DNA into host cells. Gene transfer can result in transient expression of non-integrated transferred DNA, extra chromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized regions found at each end of the AAV genome which function together in cis as origins of DNA replication and as packaging signals for the viral genome. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, *Human Gene Therapy* 5:793–801 (1994); Berns, *Parvoviridae and their Replication, in Fundamental Virology* (B. N. Fields and D. M. Knipe eds., 2d ed. 1991), for the AAV-2 sequence. As used herein, an "AAV ITR" need not have the wild-type nucleotide sequence depicted in the previously cited references, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are collectively required to replicate the viral genome and to insert the viral genome into a host genome during latent infection, or functional homologues thereof such as the human herpesvirus 6 (HHV-6) rep gene which is also known to mediate AAV-2 DNA replication. Thomson et al., *Virology* 204:304–311 (1994).

Thus, the rep coding region includes at least the genes encoding for AAV Rep 78 and Rep 68 (the "long forms of Rep"), and Rep 52 and Rep 40 (the "short forms of Rep"), or functional homologues thereof. For a further description of the AAV rep coding region, see e.g., Muzyczka, *Current Topics in Microbiol. and Immunol.* 158:97–129 (1992); Kotin, *Human Gene Therapy* 5:793–801 (1994). The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

By "AAV cap coding region" is meant the art-recognized region of the AAV genome which encodes the coat proteins of the virus which are collectively required for packaging the viral genome. Thus, the cap coding region includes at least the genes encoding for the coat proteins VP1, VP2 and VP3. For a further description of the cap coding region, see, e.g., Muzyczka, *Current Topics in Microbiol. and Immunol.* 158:97–129 (1992); Kotin, *Human Gene Therapy* 5:793–801 (1994). The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include the rep and cap coding regions. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al., *J. Virology* 63:3822–3828 (1989); McCarty et al., *J. Virology* 65:2936–2945 (1991). A number of other vectors have described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus and vaccinia virus.

For example, adenovirus-derived accessory functions have been widely studied, and a number or adenovirus genes involved in accessory functions have been identified and partially characterized. See, e.g., Carter, *Adeno-Associated Virus Helper Functions, in I CRC Handbook of Parvoviruses* (P. Tijssen ed., 1990); Muzyczka, *Curr. Topics. Microbiol and Immun.* 158:97–129 (1992). Specifically, early adenoviral gene regions E1A, E2A, E4, VAI RNA and, possibly, E1B are thought to participate in the accessory process. Janik et al., *Proc. Natl. Acad. Sci. USA* 78:1925–1929 (1981). Herpesvirus-derived accessory functions have been described. See, e.g., Young et al., *Prog. Med. Virol.* 25:113 (1979). Vaccinia virus-derived accessory functions have also been described. See, e.g., Carter (1990), supra; Schlehofer et al., *Virology* 152:110–117 (1986).

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

By "capable of supporting efficient rAAV virion production" is meant the ability of an accessory function vector or system to provide accessory functions that are sufficient to complement rAAV virion productions in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferable equal to, or greater than, the amount obtained using adenovirus infection.

By "recombinant virus" is meant a virus that has been genetically altered, e.g., by the addition or insertion of heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisnese" strands, can be packaged into any one AAV virion and both strands are equally infectious.

A "recombinant AAV virion," or "rAAV virion" is defined herein as an infectious, replication-defective virus composed of an AAV protein shell, encapsulating a heterologous nucleotide sequence of interest that is flanked on both sides by AAV ITRs. A rAAV virion is produced in a suitable host cell comprising an AAV vector, AAV helper functions and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., *Virology* 52:456 (1973); Sambrook et al., *Molecular Cloning: A Laboratory Manual* (1989); Davis et al., *Basic Methods in Molecular Biology* (1986); Chu et al., *Gene* 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The terms "promoter" and "promoter region" are used herein in their ordinary sense to refer to a DNA regulatory sequence to which RNA polymerase binds, initiating transcription of a downstream (3' direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

The term "small molecule-regulated promoter" refers to inducible promoters that are responsive to small molecules. Several small molecule-regulated promoters function in mammalian cells including, e.g., promoters that are induced or repressed by (1) the insect hormone ecdysone or its analog ponasterone A; (2) tetracycline and its derivatives; (3) RU486; and (4) rapamycin and its derivatives. "Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated," when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art. "Homology" refers to the percent identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN. Dayhoff, in *Atlas of Protein Sequence and Structure* 5:Suppl. 3 (National Biomedical Research Foundation, Washington, D.C., 1978). Preferably, default parameters are used for alignment. One alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferable at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2A gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

The phrase "lacking an intact coding region" refers to a nucleotide sequence that either completely lacks the specified coding region or that contains a non-functional coding region. For example, the phrase "an adenovirus E1B region lacking an intact E1B55k coding region" encompasses a nucleotide sequence containing an E1B region in which the E1B55k coding region has been rendered non-functional by one or more mutations, such that the E1B55k coding region no longer codes for a functional E1B55k protein. As is known in the art, such mutations may include deletion of all or part of the E1B55k coding region, one or more point mutations of the E1B55k coding region, or deletion or substitution of nucleotides that alter the reading frame of the E1B55k coding region (i.e., frameshift mutations).

Likewise, the phrase "lacks an intact AAV p5 promoter region" refers to a nucleotide sequence that either lacks a p5 promoter region or that contains a non-functional p5 promoter region. For example, the phrase encompasses a nucleotide sequence containing a p5 promoter region that has been rendered non-functional by one or more mutations, such that the p5 promoter region no longer functions in transcriptional initiation. As is known in the art, such mutations may include deletion of all or part of the p5 promoter region or one or more point mutations of the p5 promoter region.

General Methods

Central to the present invention is the identification of the minimal subset of adenovirus genes required to provide accessory functions and the subsequent development of accessory function systems which allow for the efficient production of rAAV virions in the absence of infection with a helper virus. The invention also provides accessory function systems which can be regulated, thereby reducing cytotoxic effects of various accessory proteins. Thus, accessory functions are provided by introducing one or more vectors, such as plasmids, which contain genes required for complementing rAAV virion production, into a host cell. In this manner, the present accessory function systems can support the production of commercially significant levels of rAAV virions without significant levels of contaminating helper virus particles, or other contaminating virus products (e.g., the adenoviral fiber protein). In addition, intracellular levels of the accessory proteins can be regulated, reducing cytotoxic effects. Efficient production of rAAV virions is achieved using the vectors and methods described herein.

The invention also provides methods for producing rAAV in which an AAV rep coding region and AAV vector sequences are introduced into a suitable host cell. The host cell is thereafter infected with a recombinant helper virus that provides accessory functions and an AAV cap coding region. The host cell is then cultured to produce rAAV virions. AAV vector sequences may be introduced by standard transfection methods. In the alternative, AAV vector sequences may be introduced by infection by a recombinant virus, for example, by a recombinant AAV virion. In certain embodiments, the AAV vector sequences are episomal. In other embodiments, the AAV vector sequences are integrated into the host cell genome. The recombinant helper virus may be a recombinant adenovirus, which may be engineered such that the AAV cap coding region replaces the adenoviral E3 region. In certain embodiments, the cap coding region is linked to a heterologous promoter, for example, an adenovirus major late promoter or an inducible promoter such as an ecdysone-inducible promoter.

The present invention also provides methods of producing rAAV virions comprising the steps of: introducing an AAV helper construct into a suitable host cell, said AAV helper construct comprising AAV coding regions that are expressed in the host cell to complement rAAV virion production in the host cell; introducing an accessory function system into the host cell, said accessory function system providing accessory functions for supporting rAAV virion production in the host cell; introducing an AAV vector by infection of the host cell; and culturing the host cell to produce rAAV virions. The AAV vector may be introduced into the host cell by infection with a recombinant AAV virion. The accessory function system may comprise an adenovirus VA RNA coding region, an adenovirus E4 ORF6 coding region, an adenovirus E2A 72kD coding region, an adenovirus E1A coding region, and an adenovirus E1B coding region. In certain embodiments, the E1B coding region lacks an intact E1B55k coding region.

The present invention also provides systems, methods, and host cells for producing rAAV in which certain accessory and helper functions are located on a nucleic acid molecule that is maintained as an episome in the host cell. For example, AAV rep and cap coding regions and an adenoviral E2A coding region may be located on an episomal nucleic acid. In certain embodiments, a system of the present invention comprises eight nucleic acids: a first nucleic acid comprising an SV40 large T-antigen coding region that is operably linked to an inducible promoter; a second nucleic acid comprising an adenovirus E1A coding region; a third nucleic acid comprising an adenovirus E1B coding region; a fourth nucleic acid comprising an Epstein-Barr virus nuclear antigen 1 coding region; a fifth nucleic acid comprising an adenovirus VA RNA coding region; a sixth nucleic acid comprising an adenovirus E4 ORF6 coding region; a seventh nucleic acid comprising AAV vector sequences; and an eighth nucleic acid comprising an AAV rep and cap coding region, an adenovirus E2A gene, an SV40 origin of replication, an Epstein-Barr virus latent origin of replication, and a selectable marker, wherein said eighth nucleic acid lacks an intact AAV p5 promoter region. These nucleic acids may be linked in various combinations. For example, as shown in FIG. 6, the first, second, third, fourth, fifth, and sixth nucleic acids may be combined in a single vector for insertion into the genome of a host cell using either targeted or random insertion methods.

In other embodiments, a system of the present invention comprises: a first nucleic acid comprising an SV40 large T-antigen coding region that is operably linked to an inducible promoter, an adenovirus E1A coding region, an adenovirus E1B coding region, an Epstein-Barr virus nuclear antigen 1 coding region, an adenovirus VA RNA coding region, an adenovirus E4 ORF6 coding region, and a selectable marker; a second nucleic acid comprising AAV vector sequences and a selectable marker; and a third nucleic acid comprising AAV rep and cap coding regions, an adenovirus E2A gene, an SV40 origin of replication, an Epstein-Barr virus latent origin of replication, and a selectable marker, wherein the third nucleic acid lacks an intact AAV p5 promoter region. In certain embodiments, the SV40 large T-antigen coding region is mutated to eliminate transforming activity. In certain embodiments, the E1A coding region is operably linked to an inducible promoter. In certain embodiments, the E4 ORF6 coding region is operably linked to an adenovirus E4 promoter. In certain preferred embodiments, the SV40 large T-antigen coding region is operably linked to an ecdysone-inducible promoter, the E1A coding region is operably linked to an ecdysone-inducible promoter, and the second nucleic acid further comprises ecdysone receptor subunit coding regions. In certain embodiments, the E2A coding region is operably linked to an ecdysone-inducible promoter.

The present invention also provides methods of producing rAAV comprising the steps of: introducing a first nucleic acid comprising an adenovirus VA RNA coding region and an E4 ORF6 coding region into a host cell, wherein the host cell comprises an adenovirus E1A coding region and an adenovirus E1B coding region; introducing a second nucleic acid comprising AAV vector sequences into the host cell; and introducing a third nucleic acid comprising AAV rep and cap coding regions and an adenovirus E2A coding region into the host cell such that the third nucleic acid is maintained as an episome in the host cell; wherein these steps may be performed in any order. In certain embodiments, a method of the present invention further comprises the step of introducing a fourth nucleic acid comprising a viral nuclear antigen coding region into the host cell and wherein the third nucleic acid further comprises a viral origin of replication, such that the viral nuclear antigen and viral origin of replication function to maintain the third nucleic acid as an episome in the host cell. In certain preferred embodiments, the viral nuclear antigen is SV40 large T-antigen and the viral origin of replication is an SV40 origin of replication. In certain other embodiments, the viral nuclear antigen is Epstein-Barr virus nuclear antigen 1 (EBNA1) and the viral origin of replication is ori P. In certain preferred embodiments, both viral systems (i.e., SV40 and Epstein-Barr) are included. The advantages of such a system are discussed in Example 5.

The present invention provides accessory functions, which may be provided on one or more vectors. The vector(s) include adenoviral-derived nucleotide sequences necessary for rAAV virion production. As explained further below, the sequences present on the accessory function construct(s) will be determined by the host cell used and can include E1A, E1B, E2A, E4 and VA RNA regions.

While not being bound by any particular theory, the accessory functions provided by the adenovirus, E1B, E2A, and E4 early genes are thought to be required in AAV DNA replication.

The accessory functions provided by the adenovirus E1B, E4 and VA RNA gene regions appear to participate in post transcriptional or translational events in the AAV life cycle. In regard to the accessory functions provided by E4, only the E4 34 kD protein encoded by open reading frame 6 (ORF 6) of the E4 coding region is clearly required for AAV replication. The accessory functions provided by the adenovirus gene region E1A are thought to be required as modulators to activated transcription or expression of the other adenovirus gene regions, including E1B, E2A, E4 and VA RNA.

The accessory function vectors of the invention can alternatively include one or more polynucleotide homologues which replace the adenoviral gene sequences, so long as each homologue retains the ability to provide the accessory functions of the replaced adenoviral gene. Thus, homologous nucleotide sequences can be derived from another adenoviral serotype (e.g., adenovirus type-2), from another helper virus moiety (e.g., a herpesvirus or vaccinia virus), or can be derived from any other suitable source.

Further, accessory function vectors constructed according to the invention can be in the form of a plasmid, phage, transposon or cosmid. Alternatively, the vector can be in the form of one or more linearized DNA or RNA fragments which, when associated with the appropriate control elements and enzymes, can be transcribed or expressed in a host cell to provide accessory functions. All of the above-described vectors can be readily introduced into a suitable host cell using transfection techniques that are known in the art. Such transfection methods have been described, including calcium phosphate co-precipitation (Graham et al., *Virology* 52:456–467 (1973)), direct micro-injection into cultured cells (Capecchi, *Cell* 22:479–488 (1980)), electroporation (Shigekawa et al., *Bio Techniques* 6:742–751 (1988)), liposome mediated gene transfer (Mannino et al., *Bio Techniques* 6:682–690 (1988)), lipid-mediated transfection (Felgner et al., *Proc. Natl. Acad. Sci. USA* 84:7413–7417 (1987)), and nucleic acid delivery using high-velocity microprojectiles (Klein et al., *Nature* 327:70–73 (1987)).

Accessory function vectors can be engineered using conventional recombinant techniques. Particularly, nucleic acid molecules can be readily assembled in any desired order by inserting one or more accessory function nucleotide sequences into a construct, such as by ligating restriction fragments into a cloning vector using polylinker oligonucleotides or the like. The newly formed nucleic acid molecule can then be excised from the vector and placed in an appropriate expression construct using restriction enzymes or other techniques that are well known in the art.

More particularly, selected adenoviral genes or gene regions (e.g., E1A, E1B, E2A, E4 and VA RNA), or functional homologues thereof, can be excised from a viral genome, or from a vector containing the same, and inserted into a suitable vector either individually, or linked together, to provide an accessory function construct using standard ligation techniques such as those described in Sambrook et al., supra. One such construct can be engineered to include, for example, four nucleic acid molecules derived from the adenovirus type-5 genome: a VA RNA- containing region; an E2A-containing region; an E4-containing region; and an E1A- and E1B- containing region. Ligation conditions can be empirically determined. Such conditions can typically be accomplished in 20 mM Tris-Cl pH 7.5, 10 mM MgCl$_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (weiss) units T4 DNA ligase at 14° C. (for "blunt end" ligation). Intermolecular "sticky end" ligations are usually performed at 30–100 µg/ml total DNA concentrations (5–100 nM total end concentration). The assembled molecule can then be readily inserted into an expression vector which is capable of transferring the accessory function construct between cells.

Accessory functions can also be provided by an accessory function vector system comprising more than one vector. Each vector of the system carries one or more of the necessary sequences encoding accessory function. For example, one such accessory function system could be made up of two vectors, one carrying polynucleotides encoding adenovirus VA RNAs and E4 ORF6 and one carrying polynucleotides encoding E2A72 kDa protein, E1A protein and E1B55k protein. Another system could comprise five vectors, each carrying one polynucleotide listed above. Alternatively, a system of three vectors could be used, where on vector carries one sequence encoding a necessary Ad gene, the second carries one or more of these genes and the third vector carries the remaining necessary genes. Other combinations of vectors useful in such systems can be readily devised and constructed by one of skill in the art in view of the teachings herein.

In the alternative, nucleic acid molecules comprising one or more accessory functions can be synthetically derived, using a combination of solid phase direct oligonucleotide synthesis chemistry and enzymatic ligation methods which are conventional in the art. Synthetic sequences may be constructed having features such as restriction enzyme sites, and can be prepared in commercially available oligonucleotide synthesis devices such as those devices available from Applied Biosystems, Inc. (Foster City, Calif.) using the phosphoramidite method. See, e.g., Beaucage et al., *Tetrahedron Lett.* 22:1859–1862 (1981). The nucleotide sequence of the adenovirus type-2 genome is generally known, and is publicly available (e.g., as GeneBank Reference Name: ADRCG, Accession Number: J01917; and as NCBI Identification Number: 209811). The nucleotide sequence of the adenovirus type-5 genome is believed to be 99% homologous to the adenovirus type-2 genome. Preferred codons for expression of the synthetic molecule in mammalian cells can also be readily synthesized. Complete nucleic acid molecules are then assembled from overlapping oligonucleotides prepared by the above methods. See, e.g., Edge, *Nature* 292:756 (1981); Nambair et al., *Science* 223:1299 (1984); Jay et al., *J. Biol. Chem.* 259:6311 (1984).

When adenoviral gene regions are used in the vectors of the invention to provide accessory functions, those regions will be operably linked to control sequences that direct the transcription or expression thereof. Such control sequences can comprise those adenoviral control sequences normally associated with the gene regions in the wild-type adenoviral genome. Alternatively, heterologous control sequences can be employed where desired. Useful heterologous promoter sequences include those derived from sequences encoding mammalian genes or viral genes. Examples include, but are not limited to, homologous adenoviral promoters, the SV40 early promoter, mouse mammary tumor virus LTR promoter; adenovirus major late promoter (Ad MLP); a herpes simplex virus (HSV) promoter, a cytomegalovirus (CMV) promoter (e.g., the CMV immediate early promoter region), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In a preferred embodiment, one or more of the adenovirus coding regions are operably linked to an inducible promoter. Inducible promoters include, but are not limited to, small molecule-regulated promoters such as those of the ecdysone system. See, e.g., No et al., *Proc. Natl. Acad. Sci. USA* 93:3346–3351 (1996). Ecdysone can be induced by several agonists, for example muristerone or ponasterone. Other promoters that function in mammalian cells include promoters that are induced (or repressed) by tetracycline and its derivatives (Gossen & Bujard, *Proc. Natl. Acad. Sci. USA* 89:5547–5551 (1992)); RU486 (Wang et al., *Gene Therapy* 4:432–441 (1997)); and rapamycin and its derivatives (Rivera et al., *Nature Medicine* 2:1028–1032 (1996)).

Furthermore, the accessory function vectors of the present invention can be constructed to also include selectable markers. Suitable markers include genes which confer antibiotic resistance or sensitivity, impart color, or change the antigenic characteristics when cells which have been transfected with the nucleic acid constructs are grown in an appropriate selective medium. Particular selectable marker genes useful in the practice of the invention include the Neomycin resistance gene (encoding Aminoglycoside phsphotransferase (APH)) that allows selection in mammalian cells by conferring resistance to G418 (available from Sigma, St. Louis, Mo.) and the Hygromycin-B resistance gene (encoding Hygromycin-B-phsosphotransferase (HPH)) that confers resistance to Hygromycin-B. Other suitable markers are known to those of skill in the art.

Accessory function vectors containing a full complement of the adenoviral accessory function genes or gene regions (e.g., E1A, E1B, E2A, E4, VA RNA, and/or functional homologues thereof) can be used to supply accessory functions to a host cell, including those cells not permissive for helper viruses (e.g., not injectable by a helper virus such as an adenovirus or not capable of supporting helper virus replication). In this manner, rAAV virion production can be carried out in a wide range of host cells, including those which were previously refractive to supporting such production.

In the alternative, accessory function vectors can be constructed to contain less than a full complement of accessory functions. Such vectors can be used in a cell that is already capable of supplying one or more accessory functions, for example, in a cell that supplies one or more accessory functions either inherently (e.g., where the cell expresses an accessory function homologue) or due to a transformation event. Accessory function vectors containing less than a full complement of accessory functions can also be used in combination with other ancillary accessory function constructs. It is intended, though not always specifically stated, that the accessory functions be carried on the same vector or, alternatively, on more than one vector in any combination.

Thus, in a preferred embodiment, the accessory function vectors include only the minimal subset of Ad genes required for virion production. As described in the Examples, the present inventors have determined that, within the E1 region, E1A and E1B19k strongly contribute to vector production. E1B55k, previously reported by Samulski et al., supra to be required for vector production, contributes only weakly. This finding is of particular significance because the interaction of E1B55k and E4ORF6 (which is also required for vector production) is cytotoxic to cells. Therefore, by eliminating the need to use E1B55k, cytotoxic effects on the host cell packaging line are greatly reduced.

In another aspect, suitable host cells can be engineered using ordinary recombinant techniques to produce cells that provide one or more accessory functions. For example, the human cell line 293 is a human embryonic kidney cell line that has been transformed with adenovirus type-5 DNA fragments (Graham et al., *J. Gen. Virol.* 36:59 (1977)), and expresses the adenoviral E1A and E1B genes (Aiello et al., *Virology* 94:460 (1979)). The 293 cell line is readily transfected, and provides a particularly convenient platform in which to produce rAAV virions. Thus, in one particularly preferred embodiment of the invention, an accessory function vector is provided having only the adenoviral E2A, E4 and VA RNA gene regions, or functional homologues thereof.

These vectors can be constructed as described above using recombinant and/or synthetic techniques, and can include a variety of ancillary components such as heterologous promoter regions, selectable markers and the like. Upon transfection into a host 293 cell, the vectors provide accessory functions that are capable of supporting efficient rAAV virion production.

Once engineered, the accessory function vectors of the present invention can be used in a variety of systems for rAAV virion production. For example, suitable host cells that have been transfected with one or more accessory function vectors are thereby rendered capable of producing rAAV virions when co-transfected with an AAV vector and an AAV helper construct capable of being expressed in the cell to provide AAV helper functions.

The AAV vector, AAV helper construct and the accessory function vector(s) can be introduced into the host cell, either simultaneously or serially, using transfection techniques described above.

AAV vectors used to produce rAAV virions for delivery of a nucleotide sequence of interest can be constructed to include one or more heterologous nucleotide sequences flanked on both ends (5' and 3') with functional AAV ITRs. In the practice of the invention, an AAV vector generally includes at least one AAV ITR and an appropriate promoter sequence suitably positioned relative to a heterologous nucleotide sequence, and at least one AAV ITR positioned downstream of the heterologous sequence. The 5' and 3' ITRs need not necessarily be identical to, or derived from, the same AAV isolate, so long as they function as intended.

Suitable heterologous nucleotide sequences for use in AAV vectors include any functionally relevant nucleotide sequence. Thus, AAV vectors for use in the practice of the invention can include any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include, but are not limited to, those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, or the like. A number of antisense oligonucleotides (e.g., short oligonucleotides complementary to sequences around the translation initiation site (AUG codon) of an mRNA) that are useful in antisense therapies for cancer, cardiovascular, and viral diseases have been described in the art. See, e.g., Han et al., *Proc. Natl. Acad. Sci. USA* 83:4313–4317 (1991); Uhlmann et al., *Chem. Rev.* 90:543–584 (1990); Helene et al., *Biochim. Biophys. Acta.* 1049:99–125 (1990); Agarwal et al., *Proc. Natl. Acad. Sci. USA* 85:7079–7083 (1988); Heikkila et al., *Nature* 328:445–449 (1987). For a discussion of suitable ribozymes, see, e.g., Cech et al., *J. Biol. Chem.* 267:17479–17482 (1992) and U.S. Pat. No. 5,225,347 to Goldberg et al.

AAV vectors can also include control sequences, such as promoter and polyadenylation sites, as well as selectable markers or reporter genes, enhancer sequences, and other control elements which allow for the induction of transcription. Such AAV vectors can be constructed using techniques well known in the art. See, e.g., U.S. Pat. No. 5,173,414; International Publication Numbers WO 92/01070 (published 23 Jan. 1992) and WO 93/03769 (published 4 Mar. 1993); Lebkowski et al., *Molec. Cell. Biol.* 8:3988–3996 (1988); Vincent et al., *Vaccines* 90 (Cold Spring Harbor Laboratory Press, 1990); Carter, *Current Opinion in Biotechnology* 3:533–539 (1992); Muzyczka, *Current Topics in Microbiol. and Immunol.* 158:97–129 (1992); Kotin, *Human Gene Therapy* 5:793–801 (1994); Shelling & Smith, *Gene Therapy* 1:165–169 (1994); and Zhou et al., *J. Exp. Med.* 179:1867–1875 (1994).

In the methods of the invention, AAV helper constructs are used to complement AAV functions deleted from an AAV vector. A number of suitable AAV helper constructs have been described, including, e.g., the plasmids pAAV/Ad and pIM29+45 which encode both rep and cap expression products. See, e.g., Samulski et al., *J. Virol.* 63:3822–3828 (1989); McCarty et al., *J. Virol.* 65:2936–2945 (1991). Complementing AAV helper functions in this manner to support rAAV virion production is an art-accepted technique. However, due to homologous recombination events between the AAV ITR sequences present in the AAV vector and the AAV helper function sequences present in the helper construct, such techniques also generate contaminating wild-type AAV virions in the rAAV virion stocks. The presence of wild-type AAV particles in AAV-based vector systems could potentially lead to unintentional spread of recombinant AAV virions and may interfere with the efficient expression of foreign genes.

EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Efforts have been made to ensure accuracy with respect to numbers used (e.g., amounts, temperatures, etc.), but one of skill in the art would, of course, allow for some experimental error and deviation.

Example 1

Dissection of the Adenovirus E1 Region

Plasmid Construction pBR322E1: Plasmid pBR322 E1 was constructed as follows. A 5785 bp AflIII E1-encoding fragment, corresponding to positions 142–5927 of adenovirus-2 was subcloned into the AflIII site of pBR322. Gene-specific truncations and deletions were made in the four reading E1 open reading frames encoded by this fragment. The numbers used to describe the positions of the mutations correspond to the locations of these sites in the adenovirus-2 sequence.

E1A alterations: Truncations and deletion mutants of the E1A region were constructed as follows. For the plasmid pE1A825stop, synthetic DNA encoding stop codons in all six frames were inserted into the BspEI site at position 825 of adenovirus-2. The sequences of the two oligos were CCGGACTAATTAACTAGT (SEQ ID NO: 1) and CCGGACTAGTTAATTAGT (SEQ ID NO:2). For plasmid pE1A608–930del, the sequence between the BstXI sites at positions 608 and 930 of pBR322E1A was removed.

E1B19k alterations: Truncation and deletion mutants of the E1B19k-encoding region were constructed as follows. Plasmid E1B19k was constructed by inserting synthetic DNA encoding stop codons in all six frames into the BstEII site of pBR322E1A at position 1912. The sequences of the oligos used were GTCACCCTAATAACTAGTG (SEQ ID NO:3) and CTGACCACTAGTTAATTAGG (SEQ ID NO:4). The deletion was made between the SacI site located at positions 1767 and the BstEII site at position 1912. This deletion was identical to the deletion made by Samulski et al., *J Virology* 62:206–210 (1998). These constructs were called E1B19k1912stop and E1B19k1767–1912del respectively.

E1B55k alterations: Three truncation mutants and a single deletion mutant were constructed for the E1B55k-encoding region. Synthetic DNA encoding stop codons in all six frames were inserted, in turn, in the BsrGI site at position 2243, the HindIII site at position 2798, and the BglII site at position 3322. The oligonucleotide sets used were, respectively, CTACACTAATTAACTAGT (SEQ ID NO:5) with GTACACTAGTTAATTAGT (SEQ ID NO:6), AGCTTAAT-TAACTAGA (SEQ ID NO:7) with AGCTTCTAGT-TAATTA (SEQ ID NO:8), and GATCTTAATTAACTAGAA (SEQ ID NO:9) with GATCTTCTAGTTAATTAA (SEQ ID NO:10). The deletion was made between the HindIII site at position 2798 and the BglII site at position 3322. These constructs are referred to as E1B55k2234stop, E1B55k2798stop, E1B55k3322stop, and E1B55k2798–3322del.

Protein IX alterations: Single truncation and deletion constructs were made in the protein IX encoding region. Synthetic DNA encoding stop codons in all six frames was inserted at the SacII site at position 3815. The sequences of the oligos were GGTTAATTAACTAGAACCGC (SEQ ID NO:11) and GGTTCTAGTTAATTAACCGC (SEQ ID NO: 12). The deletion was made between the SphI site at position 3652 and the MfeI site at position 3915. These constructs were called IX3815stop and IX3652–3915del.

pW1909adhLacZ: Plasmid pW1909adhlacZ was constructed as follows. A 4723 bp SpeI-EcoRV fragment containing the AAV rep and cap encoding regions was obtained from the plasmid pGN1909 (ATCC Accession Number 69871). The pGN1909 plasmid is a high efficiency AAV helper plasmid having AAV rep and cap genes with an AAV p5 promoter region that is arranged in the construct to be downstream from its normal position (in the wild-type AAV genome) relative to the rep coding region. The 4723 bp fragment was blunt-end modified, and AscI linkers (5'-GAAGGCGCGCCTTC-3' (SEQ ID NO:13)) were ligated to the blunted ends. The resulting fragment was then ligated into the unique AscI site of pWadhlacZ and oriented such that the AAV coding sequences were arranged proximal to the bacterial origin of replication in the construct.

pV4391LacZ: pW1909adhLacZ was modified by replacement of the 1909 helper sequences with the rep and cap sequences from pHLP 1. This helper has a wild-type configuration and corresponds to base pairs 146–4735 of the wild type AAV genome. This plasmid was constructed by removal of the 1909 sequences of pW1909adhLacZ by cleavage with AscI and replacement with a linker encoding a PmeI site (CGCGCCGTTTAAACGG (SEQ ID NO: 14)). The 4398 bp, rep- and cap-encoding SmaI fragment from HLP 1 was then ligated into the PmeI site in the linker.

pladeno5: pladeno 5 is a plasmid that provides a complete set of adenovirus helper functions for AAV vector production when transfected into 293 cells. Essentially, it is composed of the E2A, E4, and VA RNA regions from adenovirus-2 and a plasmid back bone. The plasmid was constructed as follows.

pBluescript II SK+ was modified to replace the 637 bp region encoding the polylinker and alpha complementation cassette with a single EcoRV site using oligonucleotide-directed mutagenesis and the following oligonucleotide: 5'-CCG CTA CAG GCG ATA TCA GCT CAC TCA A-3' (SEQ ID NO:15). A polylinker encoding the restriction sites BamHI, KpnI, SrfI, XbaI, ClaI, Bst1107I, SalI, PmeI, and NdeI was then cloned into the EcoRV site (5'-GGA TCC GGT ACC GCC CGG GCT CTA GAA TCG ATG TAT ACG TCG ACG TTT AAA CCA TAT G-3' (SEQ ID NO:16)). Adenovirus-2 DNA was digested and restriction fragments encoding the E2A region (a 5,335 bp, KpnI-SrfI fragment corresponding to positions 22,233–27,568 of the adenovirus-2 genome) and the VA RNAs (a 731 bp, EcoRV-SacII fragment corresponding to positions 10,426–11,157 of the adenovirus-2 genome) were isolated. The E2A fragment was installed between the SalI and KpnI sites of the polylinker. An E4 region was first assembled in pBluescript II SK+ by ligating a 13,864 bp, BamHI-AvrII fragment corresponding to adenovirus-2 positions 21,606–35,470 (encoding the 5' end of the gene) and a 462 bp, AvrII and SrfI, digested PCR fragment corresponding to adenovirus-2 positions 35,371–35,833 (encoding the 3' end of the gene) between the BamHI and SmaI sites of pBluescript II SK+. The oligonucleotides used to produce the PCR fragment were designed to introduce a SrfI site at the junction where the E4 promoter and the adenovirus terminal repeat intersect and have the sequences 5'-AGA GGC CCG GGC GTT TTA GGG CGG AGT AAC TTG C-3' (SEQ ID NO:17) and ACA TAC CCG CAG GCG TAG AGA C-3' (SEQ ID NO:18). The intact E4 region was excised by cleavage with SrfI and SpeI and the 3,189 bp fragment corresponding to adenovirus-2 positions 32,644–35,833 was cloned into the E2A intermediate between the SrfI and XbaI sites. Finally, the VA RNA fragment was inserted into the Bst 1107I site after T4 polymerase-mediated blunt end modification of the SacII site. The genes in pladeno 5 are arranged such that the 5' ends of the E2A and E4 promoters abut, causing the regions to transcribe away from each other in opposite directions. The VA RNA genes, which are located at the 3' end of the E4 gene, transcribe towards the E4 gene. The plasmid is 11,619 bp in length.

Virion Production Assay

AAV LacZ vector was produced by transiently transfecting KB cells with pladeno5, pV4391LacZ, and pBR322E1 or its mutated derivatives. The effect of the disruption of the component genes of the E1 region on AAV virion production was assessed. Ten cm dishes of subconfluent KB cells were transfected by the PEI method (1.5 µg PEI/µg DNA) using 10 µg each of the three plasmids. After the eight-hour transfection period, the media was changed and cultures were incubated for another 72 hours. Freeze/thaw lysates were made in the 10 ml of culture medium and these were titered by standard infection assay (18 hours), in the presence of adenovirus-2 (moi=10), followed by X-gal staining and visual quantification of stained cells.

The results are shown in Table 1 and FIG. 1.

TABLE 1

| Construct | LacZ Titer/Plate |
| --- | --- |
| pBR322E1 | 5.00E+06 |
| pBR322 | 6.00E+04 |
| E1A825 stop | 6.00E+05 |
| E1A608-930del | 1.00E+06 |
| pE1B19k1912stop | 8.00E+04 |
| pE1B19k1767-1912del | 4.00E+04 |
| pE1B55k2234stop | 4.00E+06 |
| pE1B55k2798stop | 7.00E+06 |
| pE1B55k3322stop | 8.00E+06 |
| pE1B55k2798-3322del | 9.00E+06 |
| pIX3915stop | 4.00E+06 |
| pIX3652-3915del | 5.00E+06 |

Thus, deletions in the E1A and E1B19k genes caused approximately 1 log and 2 log reductions in virion production, respectively. Deletions in the E1B55k and protein IX genes had no effect. While not being bound by any particular theory, it appears that the E1A and E1B19k genes mediate efficient AAV virion production and that the E1B55k and protein IX genes do not. This result is surprising as it is contrary to the teachings found in the literature. Samulski and co-workers found that the E1B55k, but not the E1B19k protein, contributed to AAV virus production using adenovirus (wild-type or E1 mutant) as helper virus. Samulski & Shenk, *J. Virology* 62:206–210 (1988).

These data, in contrast to previous data, indicate that the minimum complement of adeno virus required for efficient AAV virion production are: E1A, E1B19k, the VA RNAs, E2A and E4ORF6.

Example 2

Controlled Expression of Adenovirus Gene Products

In order to modulate transcription of genes encoding cytotoxic or cytostatic Adenovirus proteins, the following experiments were conducted.

Plasmid Construction:

Plasmids p1113A and p1113B: Plasmids p1113A and B, which contain the VA RNAs, E2A, E4, rep/cap IRES GFP, PGKNeo, and the E1 region with an ecdysone-inducible E1A gene, were constructed as follows: pBluescript II SK+ (Stratagene, La Jolla, Calif.) was cut with ClaI and EcoRV and ligated to synthetic DNA composed of the following oligonucleotides: CGA TAG ATC TGT TAA CTT AAT TAA GAT ATC GTT T (SEQ ID NO:19) and AAA CGA TAT CTT AAT TAA GTT AAC AGA TCT AT (SEQ ID NO:20). This plasmid was digested with BglII and HpaI and ligated to the 491 bp, BglII fragment from pIND (Invitrogen, Carlsbad, Calif.) encoding the ecdysone promoter. The resulting plasmid was called pBSIND. This plasmid was cleaved with PmeI and a 3946 bp SspI-Eco47III fragment encoding the entire E1 region was ligated into it. A junction fragment (between the Ecd promoter and the E1A gene) was generated by PCR using pBR322E1 as template and the following PCR primers: GCC GGC TAG CAC TGA AAA TGA GAC ATA TTA TCT G (SEQ ID NO:21) and TCG TGG CAG GTA AGA TCG AT (SEQ ID NO:22). This PCR product and the last plasmid described in this paragraph were cleaved with NheI and BstE1 and ligated to one another. This plasmid was called pBSecdE1.

pBSecdE1 was assembled into a larger plasmid containing DNA fragments encoding the VA RNAs, E2A, E4, a rep/cap IRES GFP construct, and a PGKNeo selectable marker. This plasmid, called p1113, was assembled as follows: pBR322 was digested with ClaI and Eco47III and a synthetic linker was ligated to it. The sequences of the linker oligos were CGC CTA GGT TCG AAC TCG AGA ATC GAT ATC GTT TAA AGC CGG CCG CAG (SEQ ID NO:23) and GCT GCG GCC GCG TTT AAA CGA TAT CGA TTC TCG AGT TCG AAC CTA GG (SEQ ID NO:24). The resulting plasmid was cleaved with Eco47III and a 1372 bp fragment encoding a PGKNeo cassette was cloned in. This plasmid was called p322.2. p322.2 was digested with SfuI and XhoI and the 743 bp, ClaI-SalI, VA RNA fragment from pladeno5 was cloned into it. The resulting plasmid was called p322.2.5. This plasmid was digested with ClaI and EcoRV and the 4459 bp EcdE1 ClaI-EcoRV from pBSecdE1 was cloned into it to create p322.3. The addition of the rep/cap IRES GFP cassette from pH1 IRES GFP was the next step. The construction of this plasmid is described below. An oligo encoding a PacI site (GGTTAATTAACC (SEQ ID NO:25)) was installed in either the unique PmeI or HpaI sites of pH1 IRES GFP. The two resulting plasmids were digested with either PacI and PmeI or PacI and HpaI. The rep/cap IRES GFP fragments were isolated and cloned into p322.3 between the PacI and EcoRV sites. This created p322.4A and p322.4B. These plasmids are identical except for the orientation of the rep/cap IRES GFP cassette. In addition to this cassette they both contain the PGKNeo maker, the VA RNAs, and the ecdE1 gene. The 8526 bp BamHI-ClaI, E2A and E4 encoding fragment from pladeno5 was then added to both of these plasmids. The ends of this fragment were changed to NotI and PmeI sites by cloning the fragment in to following polylinker (in pBSII) in the BglII and SfuI sites, and the excising with NotI and PmeI: GTT TAA ACA GAT CTT TCG AAG C (SEQ ID NO:26) and GGC CGC TTC GAA AGA TCT GTT TAA AC (SEQ ID NO:27). It was ligated to p322.4A and B between the NotI and PmeI sites. The resulting plasmids were called p1113A and p1113B.

Plasmid PH1 IRES GFP: pH11, which is described in U.S. Pat. No. 6,001,650, was mutagenized with the following oligonucleotides to introduce NsiI and BstZ17 I sites between the AAV cap termination codon and the AAV polyadenylation site: ATC TGT AAT TGC TTA CCG GTA TGC AAA GTA TAC GTT AAT CAA TAA ACC (SEQ ID NO:28). The 1692 bp NsiI-BstZ17 I fragment encode IRES GFP from the Clontech plasmid pIRES-EGFP was ligated into these sites such that the resulting plasmid encoded Rep-Cap-IRES-GFP-bGH polyadenylation site-AAV polyadenylation site.

Plasmid pIND E2A: The 3113 bp E2A encoding SacI-NotI fragment from p3.3cE2A was cloned between the SacI and NotI sites of pIND (Invitrogen, Carlsbad, Calif.) The resulting plasmid was digested with ClaI and EcoNI and a 77 bp intron encoding fragment from p3.3.1c was ligated to it. The resulting construct, pIND E2A, encodes the ecdysone promoter, the human growth hormone first intron, the E2A gene, and the SV40 late polyadenylation site.

Effect of AAV genes on Ecysone-inducible Reporter Constructs

Subconfluent HeLa cells in 10 cm dishes were transiently transfected with ecdysone-inducible LacZ constructs pIND/LacZ (Invitrogen, Carlsbad, Calif.) or pIND (SP1)/LacZ (Invitrogen, Carlsbad, Calif.) and a plasmid encoding the subunits of the ecdysone receptor (pVgRXR)(Invitrogen, Carlsbad, Calif.), in the presence and absence of the combination of pHLP19, pladeno5, and pVhEPO. The ecdysone promoters in pIND/LacZ and pIND(SP 1)/LacZ differ by the presence of 3 SP 1 sites in the later. Two micrograms, each, of the ecdysone plasmids and 5 µg, each, of the AAV vector production plasmids were used. The transfection was done by the calcium phosphate method. See, e.g., Sambrook et al., supra. Transfection time was one hour. After transfection, the medium was replaced with unsupplemented media or with media containing 10 µM muristerone (an ecdysone agonist), and the cultures were incubated for 24 hours. The cells were then fixed, stained using X-gal, and the blue cells were quantified by light microscopy. LacZ expression was quantified indirectly as blue cells per microscope field. The results are shown in table 2 below.

TABLE 2

| Construct | Muristerone Induction | AAV production plasmids | Blue cells/field |
|---|---|---|---|
| pIND/LacZ | No | No | 2 |
| pIND/LacZ | Yes | No | 100 |
| pIND/LacZ | No | Yes | 6 |
| pIND/LacZ | Yes | Yes | 800 |
| pIND(SP1)/LacZ | No | No | 6 |
| pIND(SP1)/LacZ | Yes | No | 300 |

TABLE 2-continued

| Construct | Muristerone Induction | AAV production plasmids | Blue cells/field |
|---|---|---|---|
| pIND(SP1)/LacZ | No | Yes | 8 |
| pIND(SP1)/LacZ | Yes | Yes | 700 |

Thus, the presence of AAV production components has no inhibitory effect on muristerone induction of these promoters.

Controlled Expression of E1A and E2A Genes

Ecdysone-regulated E1A and E2A constructs were assembled as described above and assayed for helper function in the presence and absence of inducer.

The effect of ponasterone modulation of E1A transcription on AAV virion production was examined. Ponasterone, like muristerone, is an ecdysone agonist. Subconfluent HeLa cells were transiently transfected with pVgRXR, p1113A and pVlacZ using the calcium phosphate method described herein for 8 hours. The transfected cells were then cultured in the presence or absence of 10 μM ponasterone. Virion preparation and titration was done as described above.

Figure 3:
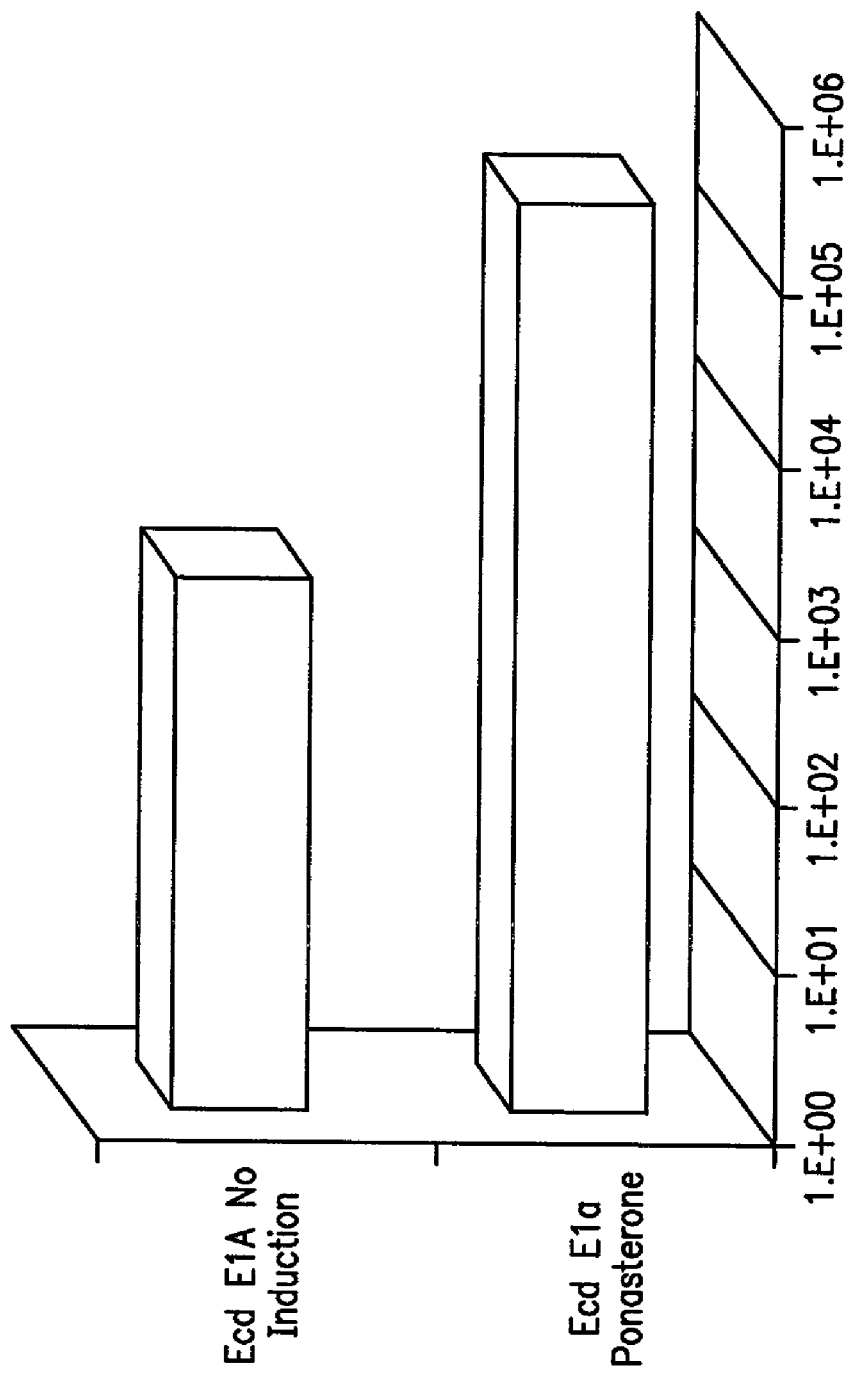
FIG. 3 depicts virion production in cells transfected with E1A constructs under the control of the ecdysone-inducible promoter. Approximately $10^2$ more virions are produced when ponasterone (an ecdysone agonist) is added to the culture media of the transfected cells.
Figure 4:
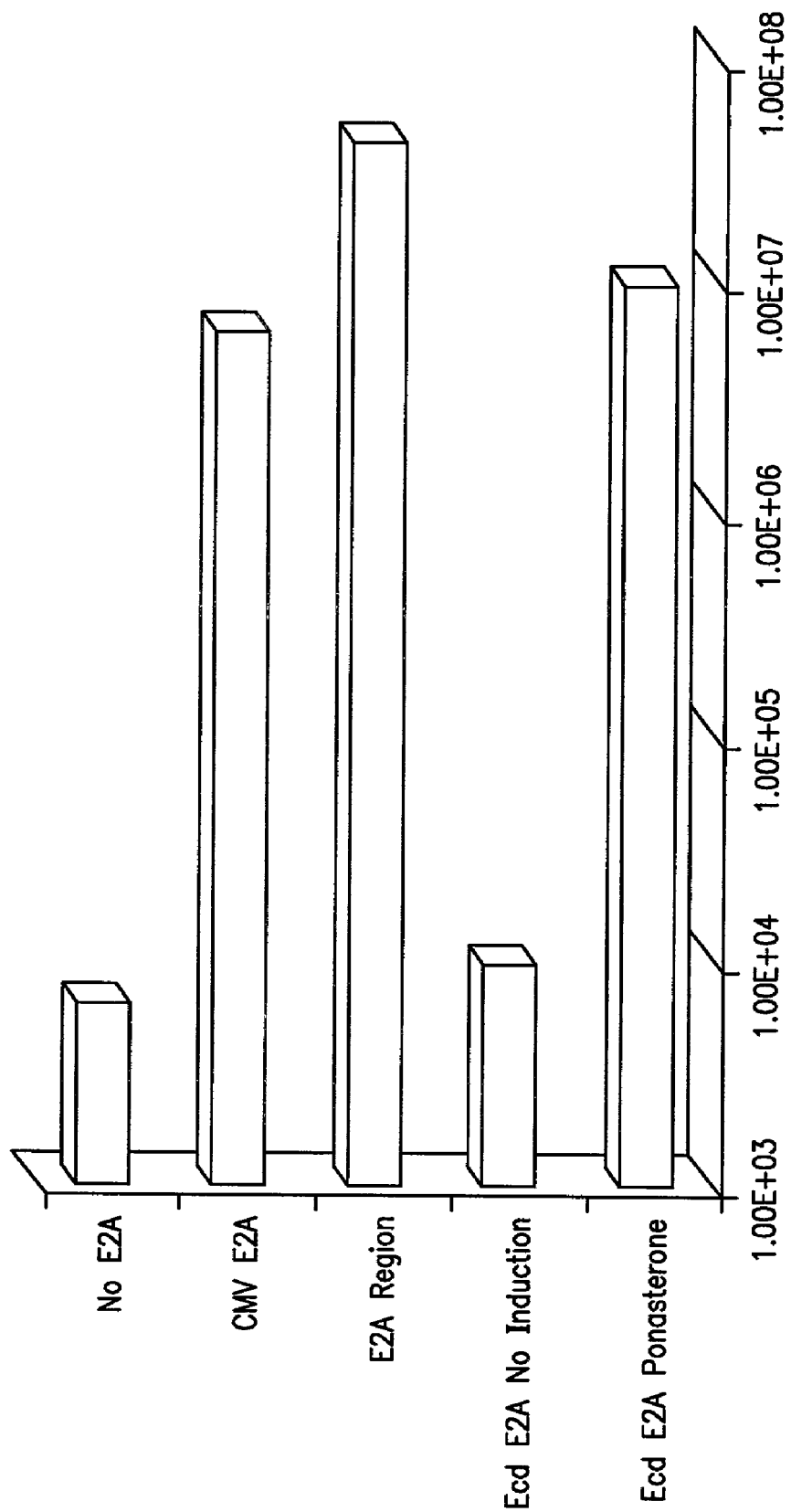
FIG. 4 depicts induction of virion production in cells transfected with constructs carrying the E2A region under the control of a CMV promoter or an ecdysone-inducible promoter. Also depicted is a negative control in which no plasmid was transfected and a positive control of wild-type E2A-containing plasmid, pladeno5. When ponasterone (an ecdysone agonist) is added to the culture media, cells transfected with the inducible-promoter E2A construct produce approximately $10^3$ more virions as compared to non-induced cells. When induced, this construct also produces approximately as many virions as the positive control.

The effect of muristerone modulation of E2A transcription on AAV virion production was also examined. 293 cells stably expressing the ecdysone receptor subunits (Invitrogen, Carlsbad Calif.) were transiently transfected with pVAE4, pVLacZ, pH1, and pIND E2A in the presence or absence of 10 μM ponasterone. p3.3cE2A (CMV E2A) and pladeno5 (E2A with an endogenous promoter) were used as positive controls. Virion preparation and titration was done as described above. The results are shown in Tables 3 and 4 below and attached FIGS. 3 and 4.

TABLE 3

Ponasterone-induced E1A: Virion production

| Plasmid | Ponasterone | LacZ Vector Titer/Plate |
|---|---|---|
| 1113A | No | $1.4 \times 10^3$ |
| 1113A | Yes | $2.3 \times 10^5$ |

TABLE 4

Ponasterone-induced E2A: Virion production

| Plasmid | Ponasterone | LacZ Vector Titer/Plate |
|---|---|---|
| No E2A plasmid | No | $6.4 \times 10^3$ |
| CMV E2A | No | $6.1 \times 10^6$ |
| pladeno5 | No | $4.1 \times 10^7$ |
| Ecd E2A | No | $9.7 \times 10^3$ |
| Ecd E2A | Yes | $9.7 \times 10^6$ |

These results show that ponasterone induction of the E1A gene in p1113A causes a 2 log increase in AAV virion production. Inclusion or exclusion of an intact E1A gene has a similar effect on AAV virion production. (See the E1 region dissection results, supra.) Ecdysone promoter constructs are also well regulated. In the absence of inducer, the virion production levels are similar to the levels produced by omitting an E2A plasmid. In the presence of inducer, virion production increases 3 logs.

Example 3

Rep-Expressing Cell Line

Figure 5:
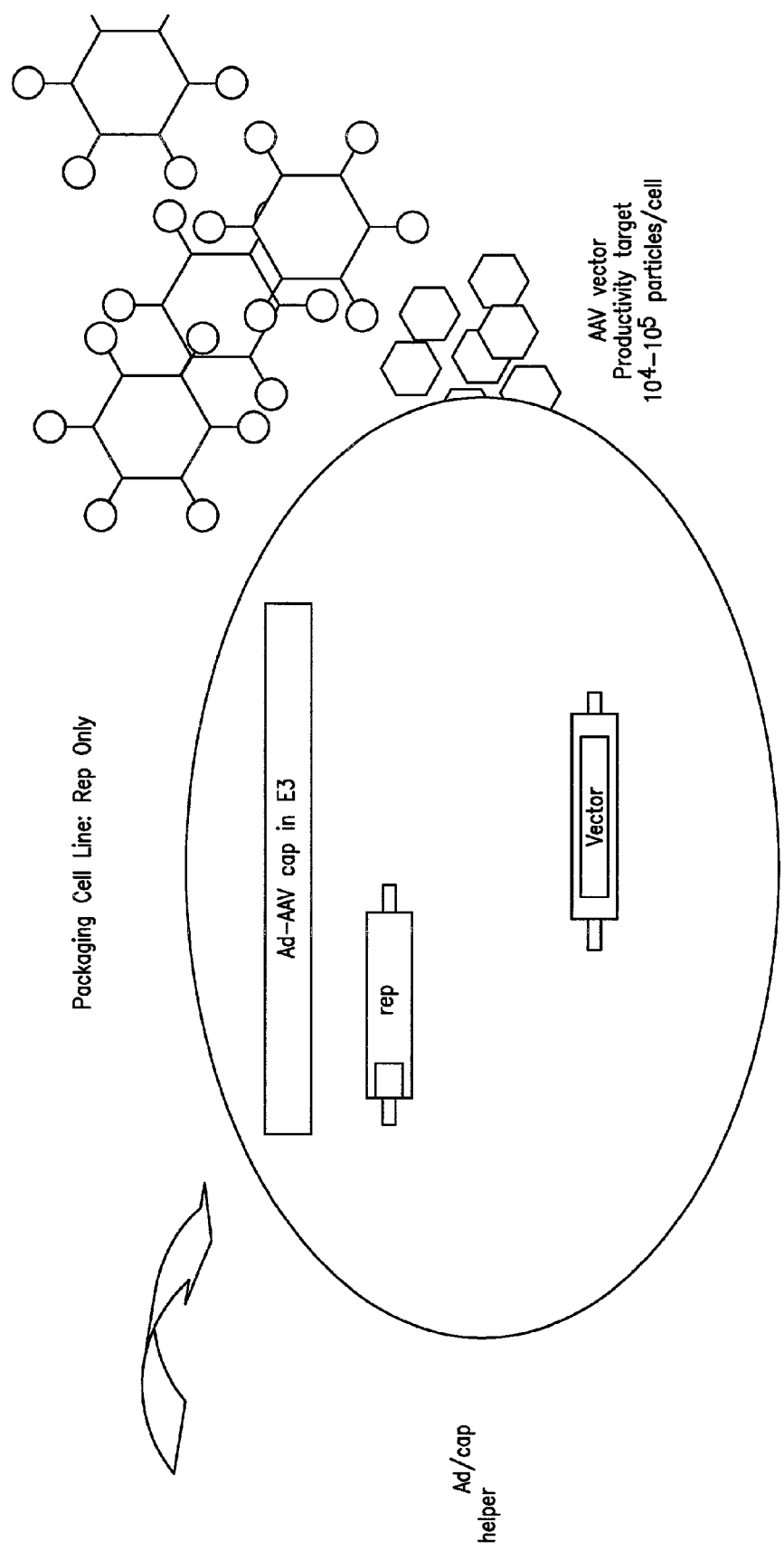
FIG. 5 schematically illustrates a system in which a Rep-expressing host cell is infected with a recombinant adenovirus carrying an AAV cap coding region to provide helper and accessory functions.

AAV vectors could be efficiently produced by a cell line stably containing the rep coding region if such a cell line was paired with a helper virus that carried the AAV cap coding region in addition to a complete set of accessory function genes. See FIG. 5. AAV vector sequences would also be necessary and could be located in the rep-containing cell line (integrated or episomal), in the helper virus, or could be introduced into the cell by infection. An example of this might be a cell line stably transfected with AAV rep and AAV vector sequences paired with an adenovirus containing the AAV cap gene replacing the adenovirus E3 region. Appropriate promoters for the AAV cap coding region might be the adenovirus major late promoter or an inducible promoter such as that induced by the ecdysone receptor (in this case, genes expressing the appropriate receptor subunits would also have to be resident in the producer cell or the helper virus). The advantage of using an inducible promoter is that cap expression could be switched off during production of the recombinant helper virus, possibly increasing the yield.

Example 4

Infection with an AAV Vector

In order to synthesize AAV vectors, AAV vector sequences must be present in the packaging cells. AAV vectors sequences are typically introduced by transfecting packaging cells with plasmids encoding them, including AAV vector sequences in helper viruses, or by stably maintaining these sequences in the cell line, either episomally, or by integrating them into the genome. As an alternative, AAV vector sequences can be provided to packaging cells by infection. In this case, a small amount of input vector is amplified by the packaging cell line.

Example 5

Producer Cell Line with Episomal Helper Genes

Packaging cell line strategies that integrate rep and cap and helper genes into the genome of the packaging cell may give low vector yields due to the low number of gene copies typically integrated by stable transfection procedures. Proteins required in high amounts for vector production, such as Cap and E2A, are produced by numerous of copies of replicating viral genomes during viral replication. AAV vector production by transfection produces high titers due to the large number (approximately 300) of helper gene plasmids transferred to the transfected cells. The small number of production gene copies integrated into the genome of a stably transfected producer cell line may not be capable of a similar synthetic capability. To address this problem, the genes that require high levels of expression (rep, cap, and E2A) may be provided to a host cell on an episome. We have devised a way to regulate the copy number of this episome and helper gene expression in this system will be regulated, at least in part, by manipulation the copy number of these genes.

An example of this approach is diagramed in FIG. 6. The producer cell has production genes integrated in the genome in two separate sites in addition to the episomal 2A and rep/cap genes. In site 1 the following genes would be integrated: an ecdysone-inducible SV40 large T-antigen gene mutated to eliminate transforming activity, an ecdysone-inducible E1A gene followed by the E1B gene driven by it's natural promoter, the EBNA1 gene, the VA RNAs, the E4ORF6 gene driven by the E4 promoter, and a selectable marker. Site 2 would contain the ecdysone receptor subunits, the AAV vector, and a selectable marker. The episome would encode the rep and cap sequences without the p5 promoter, and ecdysone inducible E2A gene, ori P, the SV40 origin and a selectable marker.

The cell line would exist in two states, a cell growth state in the absence of small molecule inducer and a production state in the presence of inducer. In the cell growth state, T-antigen, E1A and E2A production would be turned off and the episome would be maintained in the cell at low copy number per cell by an Epstein-Barr virus latent origin of replication (ori P)/Epstein-Barr virus nuclear antigen 1 (EBNA1) mechanism. The E1A-regulated P19 (small Reps), P40 (Cap), E1B19k, and E4 promoters would likewise be down-regulated. In this state vector production would be essentially shut off. Once the cell density was sufficient, a small molecule inducer such as ecdysone would be added to the media to initiate the vector production state. The inducer would result in the expression of large T-antigen, E1A and E2A. E1A expression would induce expression of E1B19k, the VA RNAs, E4ORF6, the small Reps, and Cap. Large T-antigen would initiate high level replication of the episome, resulting in a further increase in the expression of the large and small Reps, Cap, and E2A. High-level vector production should ensue.

The p5 promoter was removed from the rep/cap sequences because it has been shown that Rep binding to the optimal Rep-binding site in p5 interferes with T-antigen-mediated episomal replication. We have previously shown that rep/cap genes lacking p5 mediate high level AAV vector production when other enhancers are present on the same plasmid. The episome should mediate efficient AAV vector production, particularly at high copy number. An additional benefit of eliminating p5 is that it is not possible to generate pseudo-wild type. See U.S. Pat. No. 6,001,650. Our experience in developing a helper plasmid that does not produce detectable replication competent pseudo-wild type indicates that an intact p5 promoter is probably necessary for the production of replication competent pseudo-wild type.

Example 6

E1B19K and Functional Homologues

We have shown that the E1B19K protein plays an important role in efficient AAV vector production. Disruption of the E1B19K gene results in vector production that is deficient by as much as 100-fold. E1B19K is the viral homologue of the anti-apoptotic members of the cellular Bcl-2 family of proteins including Bcl-2 and BclXL. As part of an investigation into the mechanism of action of E1B19K, we examined the cellular homologues for helper function. Constructs expressing Bcl-2 or BclXL fully complement E1B19K mutants for vector production. These results indicate that the mechanism of E1B19K help is not specific to the viral homologue and that it may have to do with the inhibition of apoptosis.

Materials and Methods

Figure 7A:
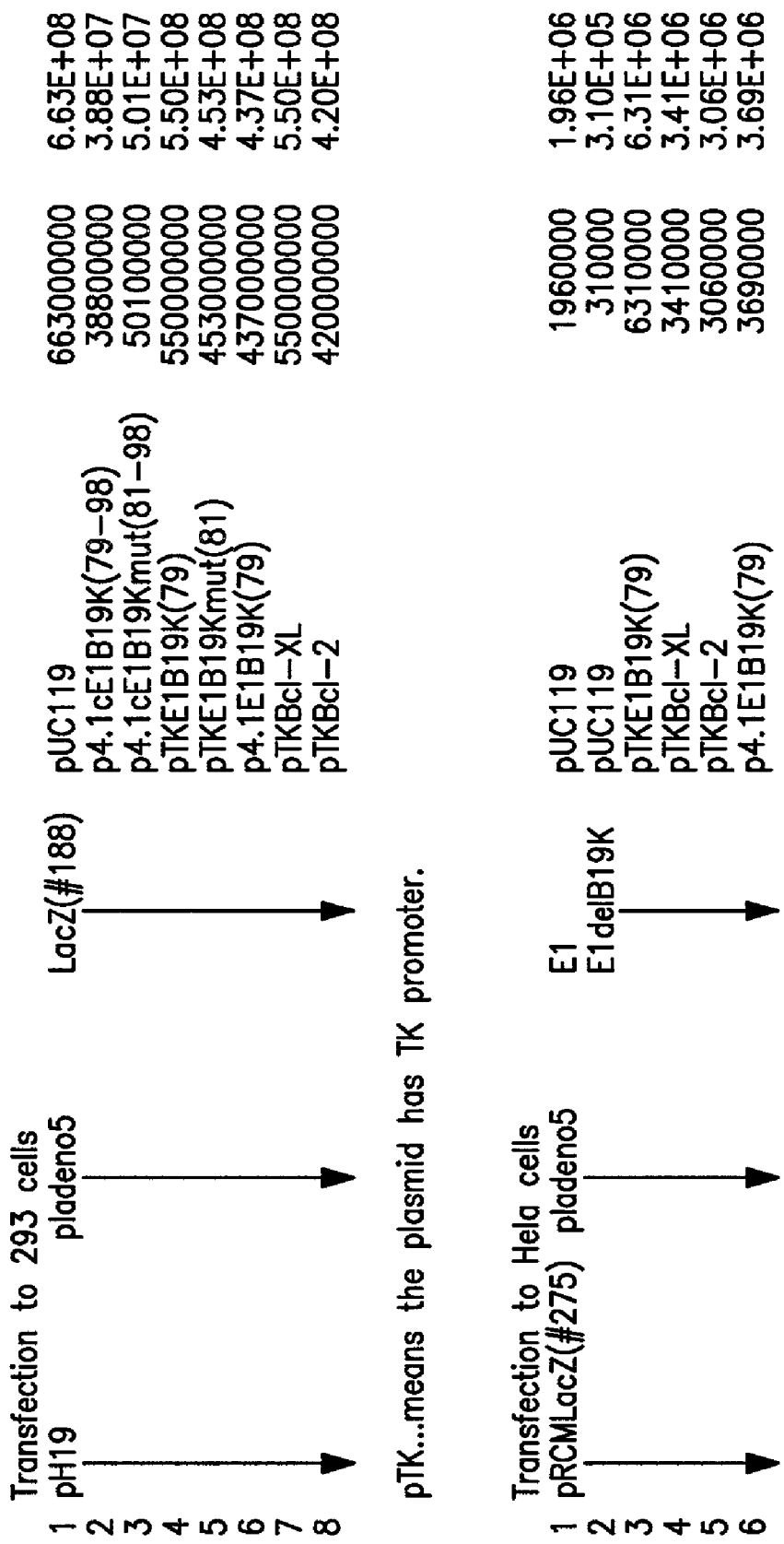
FIGS. 7A–7C depict the effect on virion production of an intact E1B coding region and complementation of this effect by genes coding for members of the Bcl-2 family.
Figure 7B:
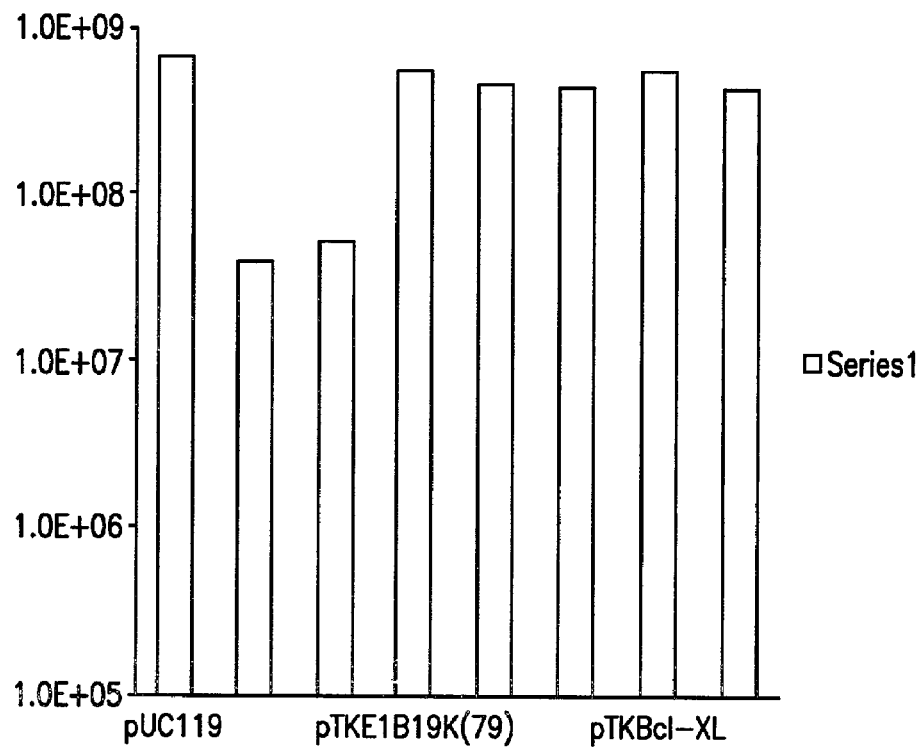
Figure 7C:
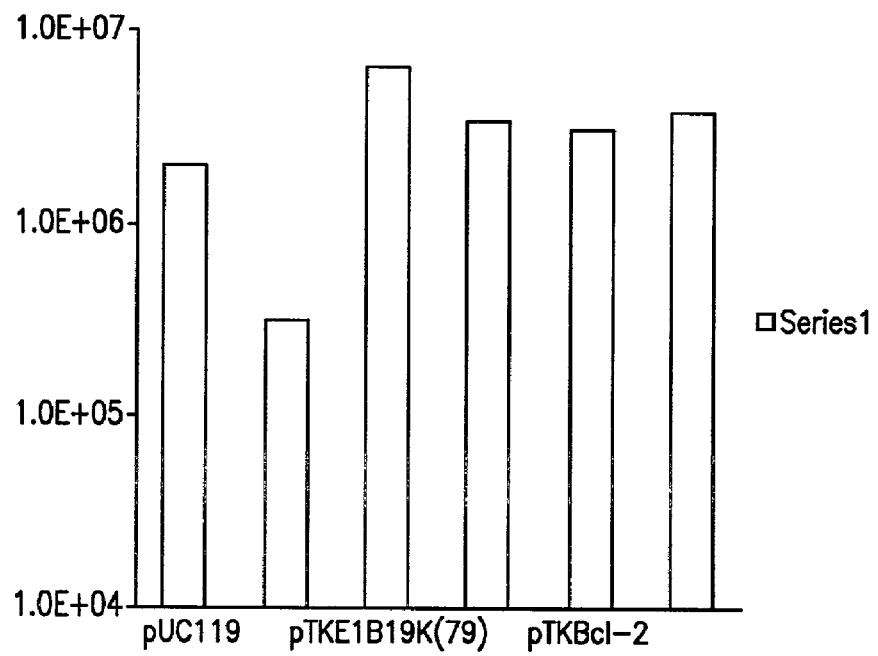

Ten-centimeter plates of HeLa cells were transfected (CaPO$_4$ method) with standard vector production plasmids. The standard production plasmids used were pVmLacZ, pH1, pladeno 5 and pE1AB. A deleted version of pE1AB, pE1delB19K, was used as an E1B19K mutant and TK promoter driven plasmids were used to express E1B 19K, BclXL, and Bcl-2. After 72 hours, the cultures were harvested and freeze/thaw lysates were prepared and titered. Titers are given in Table 5. See also FIG. 7. All transfections contained 6 µg (of each plasmid) of pHLP1, pVmLacZ, and pladeno5. Also added were the following (6 µg each): pE1AB+pUC119, pE1delB19K+pUC119, pE1delB19K+pTKE1B19K, pE1delB19K+pTKBc1Xl, or pE1delB19K+pTKBc1-2.

TABLE 5

| Gene Combinations | Titer/10 cm plate, LacZ assay |
|---|---|
| pE1AB, pUC119 | 2 × 10$^6$ |
| pE1delB19K, pUC119 | 3 × 10$^5$ |
| pE1delB19K, pTKE1B19K | 6 × 10$^6$ |
| pE1delB19K, pTKBc1X1 | 3 × 10$^6$ |
| pE1delB19K, pTKBcl-2 | 4 × 10$^6$ |

Vector production was reduced 10-fold when the E1B19K deletion plasmid was used. The loss of activity was restored by complementation with TK-driven plasmids encoding E1B19K, BclXL, or Bcl-2.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A method of producing recombinant AAV (rAAV) virions, comprising:
   (a) introducing an AAV vector into a suitable host cell;
   (b) introducing an AAV helper construct into the host cell, said helper construct comprising AAV coding regions that are expressed in the host cell to complement AAV helper functions missing from said AAV vector;
   (c) introducing an accessory function vector into the host cell, said accessory function vector providing accessory functions for supporting efficient rAAV virion production in the host cell, wherein said accessory function vector comprises a nucleic acid molecule comprising:
      (i) an adenovirus VA RNA coding region;
      (ii) an adenovirus E4 ORF6 coding region;
      (iii) an adenovirus E2A 72 kD coding region;
      (iv) an adenovirus E1A coding region; and
      (v) an adenovirus E1B region lacking an intact E1B55k coding region; and
   (d) culturing the host cell to produce rAAV virions.

2. The method of claim 1, wherein said accessory function vector is a plasmid.

3. The method of claim 2, further comprising at least one heterologous promoter region operably linked to one or more of said coding regions.

4. The method of claim 2, wherein an inducible promoter is operably linked to the E2A 72 kD coding region.

5. The method of claim 4, wherein the inducible promoter is a small molecule-regulated promoter.

6. The method of claim 5 wherein the promoter is an ecdysone-inducible promoter.

7. The method of claim 2, wherein an inducible promoter is operably linked to the E1A coding region.

8. The method of claim 7, wherein the inducible promoter is a small molecule-regulated promoter.

9. The method of claim 8, wherein the promoter is an ecdysone-inducible promoter.

10. The method of claim 1, wherein said nucleic acid molecule provides accessory functions capable of supporting efficient rAAV virion production in a human 293 host cell.

11. The method of claim 10, wherein one or more of (i)–(v) is from an adenovirus type-2 or type-5 genome.

12. The method of claim 1, wherein the nucleic acid molecule provides accessory functions capable of supporting efficient recombinant AAV (rAAV) virion production in a suitable host cell that is not infectable by adenovirus or is not capable of supporting adenovirus replication.

13. The method of claim 12, wherein one or more of (i)–(v) is from an adenovirus type-2 or type-5 genome.

14. A method of producing recombinant AAV (rAAV) virions, comprising:
   (a) introducing an AAV vector into a suitable host cell;
   (b) introducing an AAV helper construct into the host cell, said helper construct comprising AAV coding regions that are expressed in the host cell to complement AAV helper functions missing from said AAV vector;
   (c) introducing an accessory function vector into the host cell, said accessory function vector providing accessory functions for supporting efficient rAAV virion production in the host cell, wherein said accessory function vector comprises a nucleic acid molecule lacking adenoviral early gene regions E2B and E3 and comprising:
      (i) an adenovirus VA RNA coding region;
      (ii) an adenovirus E4 ORF6 coding region;
      (iii) an adenovirus E2A 72 kD coding region;
      (iv) an adenovirus E1A coding region; and
      (v) an adenovirus E1B region lacking an intact E1B55k coding region; and
   (d) culturing the host cell to produce rAAV virions.

15. The method of claim 14, wherein said accessory function vector is a plasmid.

16. A method of producing recombinant AAV (rAAV) virions, comprising:
   (a) introducing an AAV vector into a suitable host cell;
   (b) introducing an AAV helper construct into the host cell, said helper construct comprising AAV coding regions that are expressed in the host cell to complement AAV helper functions missing from said AAV vector;
   (c) introducing an accessory function vector system into the host cell, said accessory function vector system providing accessory functions for supporting efficient rAAV virion production in the host cell, wherein said accessory function vector system comprises
      (i) a nucleic acid sequence that provides adenovirus VA RNAs;
      (ii) an adenovirus E4 ORF6 coding region;
      (iii) an adenovirus E2A 72 kD coding region;
      (iv) an adenovirus E1A coding region; and
      (v) an adenovirus E1B region lacking an intact E1B55k coding region;
   wherein (i)–(v) are included on more than one accessory function vector of said system; and
   (d) culturing the host cell to produce rAAV virions.

17. The method of claim 16, wherein said accessory function vectors are plasmids.

18. A method of producing recombinant AAV (rAAV) virions comprising the steps of:
   (a) introducing an AAV helper construct into a suitable host cell, said AAV helper construct comprising AAV coding regions that are expressed in the host cell to complement rAAV virion production in the host cell;
   (b) introducing an accessory function system into the host cell, said accessory function system providing accessory functions for supporting rAAV virion production in the host cell, wherein the accessory function system comprises an adenovirus VA RNA coding region, an adenovirus E4 ORF6 coding region, an adenovirus E2A 72kD coding region, an adenovirus E1A coding region, and an adenovirus E1B coding region that lacks an intact E1B55k coding region;

(c) introducing an AAV vector by infection of the host cell with a recombinant AAV virion; and (d) culturing the host cell to produce rAAV virions.

* * * * *

SEQUENCE LISTING

<160> NUMBER OF SEQ ID NOS: 28

<210> SEQ ID NO 1
<211> LENGTH: 18
<212> TYPE: DNA
<213> ORGANISM: Artificial
<220> FEATURE:
<223> OTHER INFORMATION: oligos 1

<400> SEQUENCE: 1

-continued ccggactaat taactagt                                               18

<210> SEQ ID NO 2
<211> LENGTH: 18
<212> TYPE: DNA
<213> ORGANISM: Artificial
<220> FEATURE:
<223> OTHER INFORMATION: oligo 2

<400> SEQUENCE: 2
ccggactagt taattagt                                               18

<210> SEQ ID NO 3
<211> LENGTH: 19
<212> TYPE: DNA
<213> ORGANISM: Artificial
<220> FEATURE:
<223> OTHER INFORMATION: oligo

<400> SEQUENCE: 3
gtcaccctaa taactagtg                                              19

<210> SEQ ID NO 4
<211> LENGTH: 20
<212> TYPE: DNA
<213> ORGANISM: Artificial
<220> FEATURE:
<223> OTHER INFORMATION: oligo

<400> SEQUENCE: 4
ctgaccacta gttaattagg                                             20

<210> SEQ ID NO 5
<211> LENGTH: 18
<212> TYPE: DNA
<213> ORGANISM: Artificial
<220> FEATURE:
<223> OTHER INFORMATION: oligo

<400> SEQUENCE: 5
ctacactaat taactagt                                               18

<210> SEQ ID NO 6
<211> LENGTH: 18
<212> TYPE: DNA
<213> ORGANISM: Artificial
<220> FEATURE:
<223> OTHER INFORMATION: oglio

<400> SEQUENCE: 6
gtacactagt taattagt                                               18

<210> SEQ ID NO 7
<211> LENGTH: 16
<212> TYPE: DNA
<213> ORGANISM: Artificial
<220> FEATURE:
<223> OTHER INFORMATION: oligo

<400> SEQUENCE: 7
agcttaatta actaga                                                 16

<210> SEQ ID NO 8
<211> LENGTH: 16
<212> TYPE: DNA
<213> ORGANISM: Artificial

```
-continued

<220> FEATURE:
<223> OTHER INFORMATION: oligo

<400> SEQUENCE: 8
agcttctagt taatta                                                    16

<210> SEQ ID NO 9
<211> LENGTH: 18
<212> TYPE: DNA
<213> ORGANISM: Artificial
<220> FEATURE:
<223> OTHER INFORMATION: ologi

<400> SEQUENCE: 9
gatcttaatt aactagaa                                                  18

<210> SEQ ID NO 10
<211> LENGTH: 18
<212> TYPE: DNA
<213> ORGANISM: Artificial
<220> FEATURE:
<223> OTHER INFORMATION: oligo

<400> SEQUENCE: 10
gatcttctag ttaattaa                                                  18

<210> SEQ ID NO 11
<211> LENGTH: 20
<212> TYPE: DNA
<213> ORGANISM: Artificial
<220> FEATURE:
<223> OTHER INFORMATION: oligo

<400> SEQUENCE: 11
ggttaattaa ctagaaccgc                                                20

<210> SEQ ID NO 12
<211> LENGTH: 20
<212> TYPE: DNA
<213> ORGANISM: Artificial
<220> FEATURE:
<223> OTHER INFORMATION: oligo

<400> SEQUENCE: 12
ggttctagtt aattaaccgc                                                20

<210> SEQ ID NO 13
<211> LENGTH: 14
<212> TYPE: DNA
<213> ORGANISM: Artificial
<220> FEATURE:
<223> OTHER INFORMATION: Asc1 Linkers

<400> SEQUENCE: 13
gaaggcgcgc cttc                                                      14

<210> SEQ ID NO 14
<211> LENGTH: 16
<212> TYPE: DNA
<213> ORGANISM: Artificial
<220> FEATURE:
<223> OTHER INFORMATION: Linker encoding a Pme1 site

<400> SEQUENCE: 14
cgcgccgttt aaacgg                                                    16
```

```
<210> SEQ ID NO 15
<211> LENGTH: 16
<212> TYPE: DNA
<213> ORGANISM: Artificial
<220> FEATURE:
<223> OTHER INFORMATION: oligo

<400> SEQUENCE: 15
cgcgccgttt aaacgg                                                        16

<210> SEQ ID NO 16
<211> LENGTH: 58
<212> TYPE: DNA
<213> ORGANISM: Artificial
<220> FEATURE:
<223> OTHER INFORMATION: polylinker

<400> SEQUENCE: 16
ggatccggta ccgcccgggc tctagaatcg atgtatacgt cgacgtttaa accatatg          58

<210> SEQ ID NO 17
<211> LENGTH: 34
<212> TYPE: DNA
<213> ORGANISM: Artificial
<220> FEATURE:
<223> OTHER INFORMATION: oligo

<400> SEQUENCE: 17
agaggcccgg gcgttttagg gcggagtaac ttgc                                    34

<210> SEQ ID NO 18
<211> LENGTH: 22
<212> TYPE: DNA
<213> ORGANISM: Artificial
<220> FEATURE:
<223> OTHER INFORMATION: oligo

<400> SEQUENCE: 18
acatacccgc aggcgtagag ac                                                 22

<210> SEQ ID NO 19
<211> LENGTH: 34
<212> TYPE: DNA
<213> ORGANISM: Artificial
<220> FEATURE:
<223> OTHER INFORMATION: oligo

<400> SEQUENCE: 19
cgatagatct gttaacttaa ttaagatatc gttt                                    34

<210> SEQ ID NO 20
<211> LENGTH: 32
<212> TYPE: DNA
<213> ORGANISM: Artificial
<220> FEATURE:
<223> OTHER INFORMATION: oligo

<400> SEQUENCE: 20
aaacgatatc ttaattaagt taacagatct at                                      32

<210> SEQ ID NO 21
<211> LENGTH: 34
<212> TYPE: DNA
<213> ORGANISM: Artificial
<220> FEATURE:
<223> OTHER INFORMATION: PCR primer
```

```
<400> SEQUENCE: 21
gccggctagc actgaaaatg agacatatta tctg                                34

<210> SEQ ID NO 22
<211> LENGTH: 20
<212> TYPE: DNA
<213> ORGANISM: Artificial
<220> FEATURE:
<223> OTHER INFORMATION: PCR primer

<400> SEQUENCE: 22
tcgtggcagg taagatcgat                                                20

<210> SEQ ID NO 23
<211> LENGTH: 48
<212> TYPE: DNA
<213> ORGANISM: Artificial
<220> FEATURE:
<223> OTHER INFORMATION: linker oligo

<400> SEQUENCE: 23
cgcctaggtt cgaactcgag aatcgatatc gtttaaagcc ggccgcag                 48

<210> SEQ ID NO 24
<211> LENGTH: 47
<212> TYPE: DNA
<213> ORGANISM: Artificial
<220> FEATURE:
<223> OTHER INFORMATION: linker oligo

<400> SEQUENCE: 24
gctgcggccg cgtttaaacg atatcgattc tcgagttcga acctagg                  47

<210> SEQ ID NO 25
<211> LENGTH: 12
<212> TYPE: DNA
<213> ORGANISM: Artificial
<220> FEATURE:
<223> OTHER INFORMATION: oligo encoding a PacI site

<400> SEQUENCE: 25
ggttaattaa cc                                                        12

<210> SEQ ID NO 26
<211> LENGTH: 22
<212> TYPE: DNA
<213> ORGANISM: Artificial
<220> FEATURE:
<223> OTHER INFORMATION: polylinker

<400> SEQUENCE: 26
gtttaaacag atctttcgaa gc                                             22

<210> SEQ ID NO 27
<211> LENGTH: 26
<212> TYPE: DNA
<213> ORGANISM: Artificial
<220> FEATURE:
<223> OTHER INFORMATION: polylinker

<400> SEQUENCE: 27
ggccgcttcg aaagatctgt ttaaac                                         26

<210> SEQ ID NO 28
```

-continued

```
<211> LENGTH: 48
<212> TYPE: DNA
<213> ORGANISM: Artificial
<220> FEATURE:
<223> OTHER INFORMATION: oligo

<400> SEQUENCE: 28
atctgtaatt gcttaccggt atgcaaagta tacgttaatc aataaacc            48
```